(12) United States Patent
Wang et al.

(10) Patent No.: US 7,777,051 B2
(45) Date of Patent: Aug. 17, 2010

(54) ASYMMETRIC BENZIMIDAZOLES AND RELATED COMPOUNDS AS POTASSIUM CHANNEL MODULATORS

(75) Inventors: Xiaodong Wang, Chapel Hill, NC (US); Alan Bradley Fulp, Willow Springs, NC (US)

(73) Assignee: Icagen, Inc., Durham, NC (US)

( * ) Notice: Subject to any disclaimer, the term of this patent is extended or adjusted under 35 U.S.C. 154(b) by 594 days.

(21) Appl. No.: 10/845,287

(22) Filed: May 12, 2004

(65) Prior Publication Data

US 2005/0038067 A1  Feb. 17, 2005

Related U.S. Application Data

(60) Provisional application No. 60/470,393, filed on May 13, 2003.

(51) Int. Cl.
*A61K 31/4184* (2006.01)
*C07D 403/10* (2006.01)
*C07D 403/14* (2006.01)
(52) U.S. Cl. .................................. 548/310.7; 514/394
(58) Field of Classification Search ............... 548/310.7
See application file for complete search history.

(56) References Cited

U.S. PATENT DOCUMENTS 3,325,506 A * 6/1967 Jones et al. ................. 548/127
5,478,858 A   12/1995 Cupps et al.
7,132,439 B2 * 11/2006 Wang et al. ................. 514/393

FOREIGN PATENT DOCUMENTS

GB           2351081 A  * 12/2000
JP       2002/161084 A  *  6/2002
WO       WO 99/26933 A1    6/1999

OTHER PUBLICATIONS

Nakahira et al., CA 137:6177, 2002.*
An English translation of JP 2002/161084, 2002.*
Porai-Koshits et al., CA 38:8316, 1944.*
Brunet et al., Canadian Journal of Chemistry, 1996, 74(5), pp. 689-696.*
Korshak et al., Macromolecules (1974), 7(5), pp. 589-598.*

* cited by examiner

*Primary Examiner*—Laura L. Stockton
(74) *Attorney, Agent, or Firm*—Townsend and Townsend and Crew LLP

(57) ABSTRACT

The present invention provides a genus of asymmetric benzimidazole compounds, methods and pharmaceut1cal compositions that are useful as modulators of potassium ion channels. The compounds of the invention are of use in both therapeutic and diagnostic methods.

25 Claims, 11 Drawing Sheets

1

2

3

4

5

6

7

8

9

10

11

12

13

14

43

44

45

46

47

48

49

50

51

52

53

54

55

56

57

58

59

60

61

62

63

64

65

66

67

68

69

70

71

72

73

74

75

76

77

78

79

80

81

82

83

84

85

86

87

88

89

90

91

92

93

94

95

96

97

98

99

100

101

102

103

104

105

106

107

108

109

110

111

112

113

114

115

116

117

118

119

120

121

122

123

124

125

US 7,777,051 B2

ASYMMETRIC BENZIMIDAZOLES AND RELATED COMPOUNDS AS POTASSIUM CHANNEL MODULATORS

CROSS-REFERENCE TO RELATED APPLICATIONS

The present application claims the benefit of U.S. Provisional Patent Application Ser. No. 60/470,393, filed May 13, 2003, herein incorporated by reference in its entirety.

FIELD OF THE INVENTION

This invention relates to the use of certain asymmetric benzimidazole compounds as potassium channel modulators and to the treatment of diseases by the modulation of potassium channels. Additionally, this invention relates to novel asymmetric benzimidazole compounds that are useful as potassium channel modulators.

BACKGROUND OF THE INVENTION

Ion channels are cellular proteins that regulate the flow of ions, including calcium, potassium, sodium and chloride, into and out of cells. These channels are present in all human cells and affect such processes as nerve transmission, muscle contraction and cellular secretion. Among the ion channels, potassium channels are the most ubiquitous and diverse, being found in a variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels have now been associated with a number of physiological processes, including regulation of heartbeat, dilation of arteries, release of insulin, excitability of nerve cells, and regulation of renal electrolyte transport. Moreover, studies have indicated that $K^+$ channels are a therapeutic target in the treatment of a number of diseases including central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as active as neuroprotective agents (e.g., to prevent stroke and the like). The compounds of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

Potassium channels are made by alpha subunits that fall into at least 8 families, based on predicted structural and functional similarities (Wei et al., *Neuropharmacology* 35(7): 805-829 (1997)). Three of these families (Kv, eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94(25): 14066-14071 (1997)) and are gated by both voltage and calcium or pH (Schreiber et al., *J. Biol. Chem.* 273: 3509-3516 (1998)). Another family, the inward rectifier potassium channels (Kir), belong to a structural family containing two transmembrane domains, and an eighth functionally diverse family (TP, or "two-pore") contains two tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493: 625-633 (1996); Shi et al., *Neuron* 16(4): 843-852 (1996)). In another example, the KQT family beta subunit, minK, primarily changes activation kinetics (Sanguinetti et al., *Nature* 384: 80-83 (1996)).

Slo or BK potassium channels are large conductance potassium channels found in a wide variety of tissues, both in the central nervous system and periphery. They play a key role in the regulation of processes such as neuronal integration, muscular contraction and hormone secretion. They may also be involved in processes such as lymphocyte differentiation and cell proliferation, spermatocyte differentiation and sperm motility. Three alpha subunits of the Slo family have been cloned, i.e., Slo1, Slo2, and Slo3 (Butler et al., *Science* 261: 221-224 (1993); Schreiber et al., *J. Biol. Chem.*, 273: 3509-3516 (1998); and Joiner et al., *Nature Neurosci.* 1: 462-469 (1998)). These Slo family members have been shown to be voltage and/or calcium gated, and/or regulated by intracellular pH.

Certain members of the Kv family of potassium channels were recently renamed (see, Biervert, et al., *Science* 279: 403-406 (1998)). KvLQT1 was re-named KCNQ1, and the KvLQT1-related channels (KvLR1 and KvLR2) were renamed KCNQ2 and KCNQ3, respectively. More recently, a fourth member of the KCNQ subfamily was identified (KCNQ4) as a channel expressed in sensory outer hair cells (Kubisch, et al., *Cell* 96(3): 437-446 (1999)).

SK channels are small conductance, $Ca^{2+}$-activated $K^+$ channels that underlie neuronal slow after hyperpolarization and mediate spike frequency adaptation (Khawaled et al., *Pflugers Arch.* 438: 314-321 (1999)). SK channels are present in many central neurons and ganglia, where their primary function is to hyperpolarize nerve cells following one or several action potentials, in order to prevent the occurrence of long trains of epileptogenic activity. The SK channels are also present in several peripheral cells including skeletal muscle, gland cells, liver cells, and T-lymphocytes. The significance of SK channels in normal skeletal muscle is not clear, but their number is significantly increased in denervated muscle, and the large number of SK channels in the muscle of patients with myotonic muscle dystrophia suggests a role in the pathogenesis of the disease.

Three SK channels have been identified to date: SK1, SK2 and SK3 (Rimini et al., *Brain Res. Mol. Brain Res.* 85: 218-220 (2000)). The quantities of SK1, SK2 and SK3 expression in human brain have been measured using TaqMan RT-PCR on a range of human brain and peripheral tissue samples. SK1 expression was found to be restricted to the brain whereas SK2 and SK3 are more widely expressed.

SK channels have been shown to have a distinct pharmacological profile. For example, using patch clamp techniques, the effects on SK2 subtype channels of eight clinically relevant psychoactive compounds structurally related to the tricyclic antidepressants were investigated (Dreixler et al., *Eur. J. Pharmacol.* 401: 1-7 (2000)). The compounds evaluated included amitriptyline, carbamazepine, chlorpromazine, cyproheptadine, imipramine, tacrine and trifluperazine. Each of the compounds tested was found to block SK2 channel currents with micromolar affinity. In contrast, the cognitive enhancer linopirdine was ineffective at inhibiting SK channels. A number of neuromuscular inhibiting agents which affect SK channels exist, e.g. apamin, atracurium, pancuronium and tubocurarine (Shah et al., *Br J Pharmacol* 129: 627-630 (2000)).

Patch clamp techniques have been used to study the effect of the centrally acting muscle relaxant chlorzoxazone and three structurally related compounds, 1-ethyl-2-benzimidazolinone (1-EBIO), zoxazolamine, and 1,3-dihydro-1-[2-hydroxy-5-(trifluoromethyl)phenyl]-5-(trifluoromethyl)-2H-benzimidazol-2-one (NS 1619) on recombinant rat brain SK2 channels (rSK2 channels) expressed in HEK293 mammalian cells (Cao et al., *J Pharmacol. Exp. Ther.* 296: 683-689 (2001)). When applied externally, chlorzoxazone, 1-EBIO, and zoxazolamine activated rSK2 channel currents in cells dialyzed with a nominally $Ca^{2+}$-free intracellular solution.

The effects of metal cations on the activation of recombinant human SK4 (also known as hIK1 or hKCa4) channels has also been studied (Cao and Houamed, *FEBS Lett.* 446: 137-141 (1999)). The ion channels were expressed in HEK 293 cells, and tested using patch clamp recording. Of the nine metals tested, cobalt, iron, magnesium, and zinc did not activate the SK4 channels when applied, at concentrations up to 100 µM, to the inside of SK4 channel-expressing membrane patches. Barium, cadmium, calcium, lead, and strontium activated SK4 channels in a concentration-dependent manner. The rank order of potency was at $Ca^{2+}>Pb^{2+}>Cd^{2+}>Sr^{2+}>Ba^{2+}$.

WO 97/48705 discloses a particular group of chemical compounds useful as calcium activated potassium channel inhibiting agents. U.S. Pat. No. 5,739,127 and U.S. Pat. No. 5,760,230 discloses a series of 2,4'-bridged bis-2,4-diaminoquinazolines having activity towards apamine-sensitive potassium channels. None of the aforementioned references disclose that the compounds set forth therein exhibit any selectivity towards the SK channel.

In contrast to the compounds set forth in U.S. Pat. No. 5,922,794, the present invention provides a genus of SK channel modulators that are based on an asymmetric benzimidazole scaffold in which the benzimidazole moiety is linked through the carbon atom at position-2 of the imidazole ring system. The compounds of the invention are potent and specific modulators of SK channels.

BRIEF SUMMARY OF THE INVENTION

The present invention provides asymmetric benzimidazole compounds, which are useful in modulating potassium ion flux through voltage-dependent potassium channels, and for treating diseases through the modulation of potassium ion flux through these channels.

More particularly, the invention provides compounds, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as active as neuroprotective agents (e.g., to prevent stroke and the like). The compounds of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

In a first aspect, the present invention provides compounds having a structure according to Formula I:

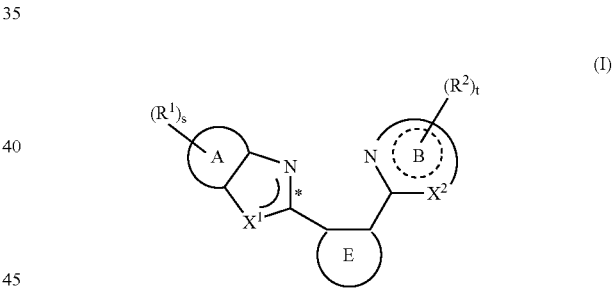

in which A is selected from 5- or 6-membered aryl and heteroaryl ring systems. The symbol B represents a group selected from 5- or 6-membered heteroaryl rings. The symbol E represents substituted or unsubstituted aryl, or substituted or unsubstituted heteroaryl ring systems. The symbols s and t are integers independently selected from 1-5. The curved line represents a double bond between C* and N or a double bond between C* and $X^1$. The symbols $R^1$ and $R^2$ represent members independently selected from H, $OR^7$, $NR^8R^9$, $NO_2$, $—SO_2NR^8R^9$, halogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, and substituted or unsubstituted heteroaryl. $R^7$, $R^8$, and $R^9$ are independently selected from hydrogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, and substituted or unsubstituted heteroaryl. $R^8$ and $R^9$ together with the atoms to which they are joined optionally form a substituted or unsubstituted 5- to 7-membered ring. If A is substituted with more than one $R^1$, then each $R^1$ is optionally different. If B is substituted with more than one $R^2$, then each $R^2$ is optionally different. $X^1$ is a member selected from $N(R^3)$, S, O, $NCH_2(R^4)$, $C(R^5)$, and $CH(R^6)$. $X^2$ is a member selected from $N(R^3)$, S, O, and $C(R^5)$. The symbols $R^3$, $R^4$, $R^5$, and $R^6$ represent groups independently selected from H, substituted or unsubstituted alkyl or substituted or unsubstituted heteroaryl.

In a second aspect, the present invention provides methods for modulating ion flow through voltage-dependent potassium channels in a cell. The method includes contacting the cell with a potassium channel-modulating amount of a compound of the invention. The cell may be in culture or in a subject in need of treatment that involves modulating ion flow through a voltage-dependent channel.

In a third aspect, the invention provides a method of treating a disorder or condition through modulation of a voltage-dependent potassium channel of the SK family. The method includes administering a therapeutically effective amount of a compound of the invention to a subject in need of such treatment.

In a fourth aspect, the invention also provides pharmaceutical compositions that include one or more compounds of the invention in combination with a pharmaceutically acceptable excipient.

Other objects, advantages and embodiments of the invention will be apparent from review of the Detailed Description that follows.

DETAILED DESCRIPTION OF THE INVENTION

Figure 1A:
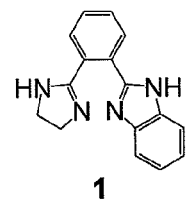
FIG. 1 displays structures of representative compounds of the invention.

Abbreviations and Definitions:

The abbreviations used herein have their conventional meaning within the chemical and biological arts. For example: CHO, Chinese hamster ovary; EBSS, Earl's Balanced Salt Solution; hSK (or SK), $Ca^{2+}$ activated small conductance potassium channels; SDS, sodium dodecyl sulfate; $Et_3N$, triethylamine; MeOH, methanol; and DMSO, dimethylsulfoxide.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Compound of the invention," as used herein refers to a compound according to Formula I, and a pharmaceutically acceptable salt of a compound according to Formula I.

"Modulating," as used herein, refers to the ability of a compound of the invention to activate and/or inhibit an SK potassium channel.

"Activate", as used herein, refers to the partial or full stimulation of an SK channel by a compound of the invention, which leads to an increase in ion flux either into or out of a cell in which an SK channel is found.

"Inhibiting" and "blocking," are used interchangeably herein to refer to the partial or full blockade of an SK channel by a compound of the invention, which leads to a decrease in ion flux either into or out of a cell in which an SK channel is found.

Where substituent groups are specified by their conventional chemical formulae, written from left to right, they equally encompass the chemically identical substituents which would result from writing the structure from right to left, e.g., —$CH_2O$— is intended to also recite —$OCH_2$—; —$NHS(O)_2$— is also intended to represent —$S(O)_2HN$—; etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'- and —R'C.(O)$_2$—.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrothien-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR"R'" R'"', —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R" R'")=NR" ", —NR—C(NR'R")=NR'", —S(O)R', —S(O)$_2$R', —S(O)$_2$NR'R", —NRSO$_2$R', —CN and —NO$_2$ in a number ranging from zero to (2m"+1), where m" is the total number of carbon atoms in such radical. R', R", R'" and R'"' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R'"' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR"R'" R'"', —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R'"' are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R'" and R'"' groups when more than one of these groups is present.

Two of the aryl substituents on adjacent atoms of the aryl or heteroaryl ring may optionally be replaced with a substituent of the formula -T-C(O)—(CRR')$_q$-U-, wherein T and U are independently —NR—, —O—, —CRR'- or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'-, —O—, —NR—, —S—, —S(O)—, —S(O)$_2$—, —S(O)$_2$NR'- or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$-X—(CR"R'")$_d$-, where s and d are independently integers of from 0 to 3, and X is —O—, —NR'-, —S—, —S(O)—, —S(O)$_2$—, or —S(O)$_2$NR'-. The substituents R, R', R" and R'" are preferably independently selected from hydrogen or substituted or unsubstituted ($C_1$-$C_6$)alkyl.

The term "alkyl amide" refers to carboxylic acid amides that are functionalized on the amide nitrogen by one or more alkyl groups as defined herein.

The term "alkyl amine" refers to amines in which the nitrogen atom is functionalized with one or more alkyl groups as defined herein.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I or carbon-14 ($^{14}$C). All isotopic variations of the compounds of the present invention, whether radioactive or not, are intended to be encompassed within the scope of the present invention.

Introduction

The development of therapeutic agents which act on potassium ion channels has received considerable recent attention. Efforts to elucidate the structure of compounds active towards the SK family of ion channels have led to the discovery of diverse species. For example, a family of N-alkyl benzamides that act by inhibiting potassium channels has been described (see, PCT/US98/02364, published as WO 98/37068). The present invention provides a family of distinct, SK-active asymmetric benzimidazoles.

The present invention provides compounds, compositions, and methods for decreasing ion flux in voltage-dependent potassium channels, particularly the channels of the small conductance, calcium activated potassium channels (e.g., hSK1, hSK2, and hSK3). The SK family of channels is implicated in a number of disorders that are targets for a therapeutic or prophylactic regimen, which functions by blockade or inhibition of one or more members of the SK channel family. The compounds of the present invention are useful to treat central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as active as neuroprotective agents (e.g., to prevent stroke and the like). The compounds of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

The compounds provided herein are shown to act as potassium channel modulators, particularly for members of the SK family of ion channels (e.g., hSK1, hSK2, and hSK3).

DESCRIPTION OF THE EMBODIMENTS

I. Modulators of Voltage-Dependent Potassium Channels

In one aspect, the present invention provides compounds having a structure according to Formula I:

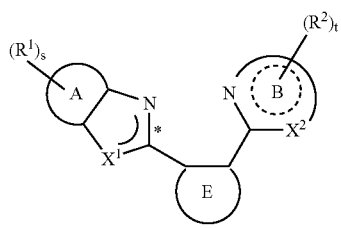

in which A is selected from 5- or 6-membered aryl and heteroaryl ring systems. The symbol B represents a group selected from 5- or 6-membered heteroaryl rings. The symbol E represents substituted or unsubstituted aryl, or substituted or unsubstituted heteroaryl ring systems. The symbols s and t are integers independently selected from 1-5. The curved line represents a double bond between C* and N or a double bond between C* and $X^1$. The symbols $R^1$ and $R^2$ represent members independently selected from H, $OR^7$, $NR^8R^9$, $NO_2$, $-SO_2NR^8R^9$, halogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, and substituted or unsubstituted heteroaryl. $R^7$, $R^8$, and $R^9$ are independently selected from hydrogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, and substituted or unsubstituted heteroaryl. $R^8$ and $R^9$ together with the atoms to which they are joined optionally form a substituted or unsubstituted 5- to 7-membered ring. If A is substituted with more than one $R^1$, then each $R^1$ is optionally different. If B is substituted with more than one $R^2$, then each $R^2$ is optionally different. $X^1$ is a member selected from $N(R^3)$, S, O, $NCH_2(R^4)$, $C(R^5)$, and $CH(R^6)$. $X^2$ is a member selected from $N(R^3)$, S, O, and $C(R^5)$. The symbols $R^3$, $R^4$, $R^5$, and $R^6$ represent groups independently selected from H, substituted or unsubstituted alkyl or substituted or unsubstituted heteroaryl.

In an exemplary embodiment, A and E are independently selected from substituted or unsubstituted phenyl and substituted or unsubstituted pyridyl ring systems.

In another exemplary embodiment, A and E are substituted with a member selected from $NH_2$, alkyl amines, aryl amines, carboxyl, esters, $C(O)NH_2$, alkyl amides, aryl amides, sulfonamides, thioureas, halogens, alkoxy, carbamate, ether, hydroxy, imides and combinations thereof.

In an exemplary embodiment, the invention provides a compound having a structure according to Formula II:

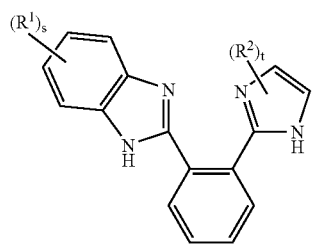

in which $R^1$ and $R^2$ are members independently selected from H, $NH_2$, alkyl amines, aryl amines, carboxyl, $C(O)NH_2$, alkyl amides, aryl amides, sulfonamides, thioureas, esters, halogens, alkoxy, carbamate, ether, hydroxy substituted or unsubstituted alkyl, ketone and combinations thereof. Two $R^1$ groups together with the atoms to which they are joined optionally form a substituted or unsubstituted 5- to 7-membered ring. Also, two $R^2$ groups together with the atoms to which they are joined optionally form a substituted or unsubstituted 5- to 7-membered ring.

In another exemplary embodiment, the invention provides a compound having a structure according to Formula III:

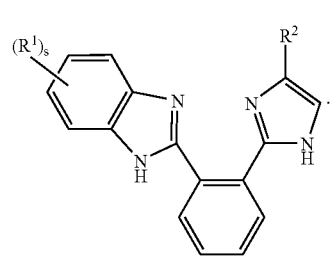

In another exemplary embodiment, the invention provides a compound having a structure according to Formula IV:

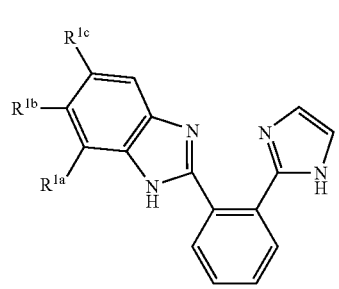

in which $R^{1a}$, $R^{1b}$, and $R^{1c}$ are members independently selected from H, $NH_2$, alkyl amines, aryl amines, carboxyl, $C(O)NH_2$, alkyl amides, aryl amides, sulfonamides, thioureas, esters, halogens, alkoxy, carbamate, ether, hydroxy substituted or unsubstituted alkyl, ketone and combinations thereof. $R^{1b}$ and $R^{1c}$ together with the atoms to which they are joined optionally form a substituted or unsubstituted 5- to 7-membered ring.

In an exemplary embodiment, $R^{1b}$ and $R^{1c}$ are combined to form an oxygen-containing heterocycle. In another exemplary embodiment, $R^{1a}$ is —OH, $R^{1b}$ is H and $R^{1c}$ is H. In still another exemplary embodiment, $R^{1a}$ is H and $R^{1c}$ are H.

In an exemplary embodiment, $R^{1b}$ is selected from H, $-NH_2$, $-OCH_3$,

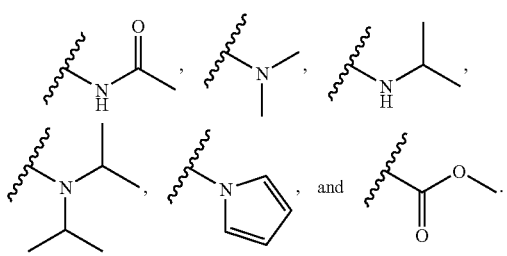

In an exemplary embodiment, the invention provides a compound having a structure according to Formula V:

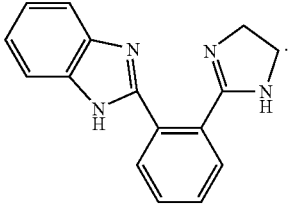
(V)

In an exemplary embodiment, the invention provides a compound having a structure according to Formula VI:

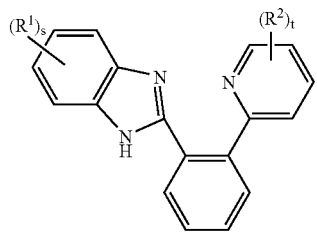
(VI)

in which $R^1$ and $R^2$ are members independently selected from H, $NH_2$, alkyl amines, aryl amines, carboxyl, $C(O)NH_2$, alkyl amides, aryl amides, sulfonamides, thioureas, esters, halogens, alkoxy, carbamate, ether, hydroxy substituted or unsubstituted alkyl, ketone and combinations thereof. Two $R^1$ groups together with the atoms to which they are joined optionally form a substituted or unsubstituted 5- to 7-membered ring. Two $R^2$ groups together with the atoms to which they are joined optionally form a substituted or unsubstituted 5- to 7-membered ring.

In an exemplary embodiment, the invention provides a compound having a structure according to Formula VII:

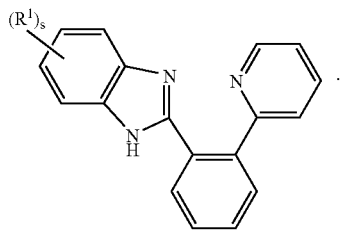
(VII)

In an exemplary embodiment, the invention provides a compound having a structure according to Formula VIII:

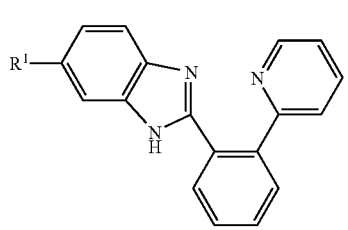
(VIII)

in which $R^1$ is selected from

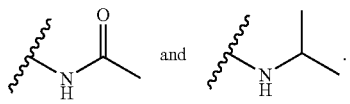

In an exemplary embodiment, the invention provides a compound having a structure according to Formula IX:

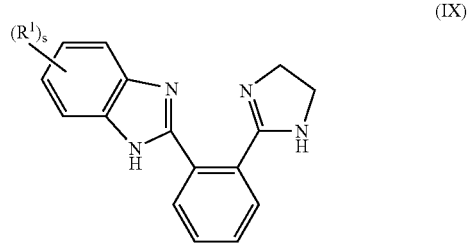
(IX)

in which $R^1$ and $R^2$ are members independently selected from H, $NH_2$, alkyl amines, aryl amines, carboxyl, $C(O)NH_2$, alkyl amides, aryl amides, sulfonamides, thioureas, esters, halogens, alkoxy, carbamate, ether, hydroxy substituted or unsubstituted alkyl, ketone and combinations thereof. Two $R^1$ groups together with the atoms to which they are joined optionally form a substituted or unsubstituted 5- to 7-membered ring. Two $R^2$ groups together with the atoms to which they are joined optionally form a substituted or unsubstituted 5- to 7-membered ring.

Figure 1A:
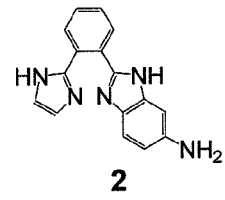
Figure 1A:
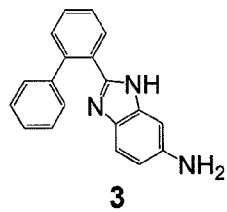
Figure 1A:
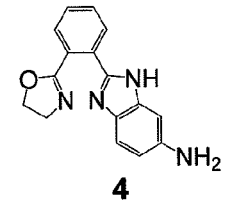
Figure 1A:
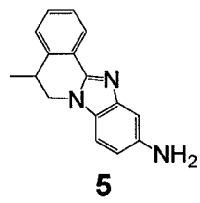
Figure 1A:
Figure 1A:
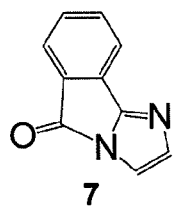
Figure 1A:
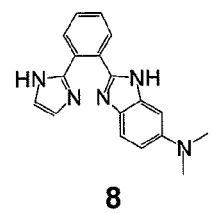
Figure 1A:
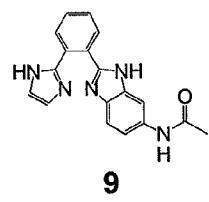
Figure 1A:
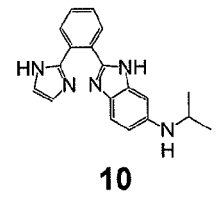
Figure 1A:
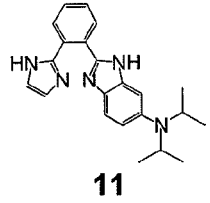
Figure 1A:
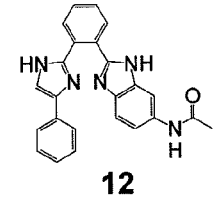
Figure 1A:
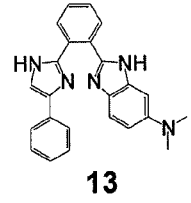
Figure 1A:
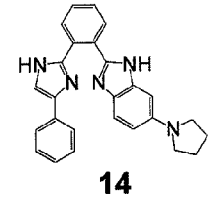
Figure 1B:
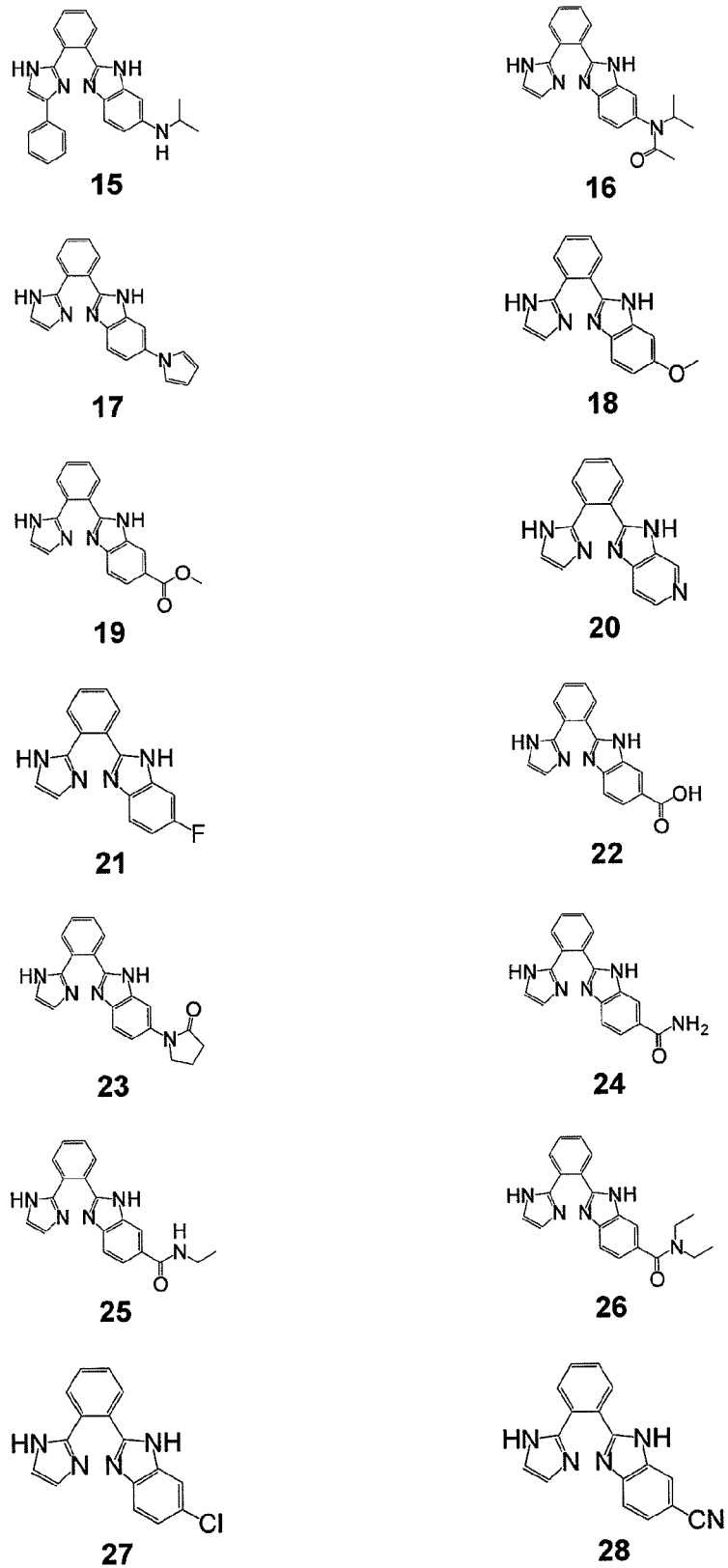
Figure 1C:
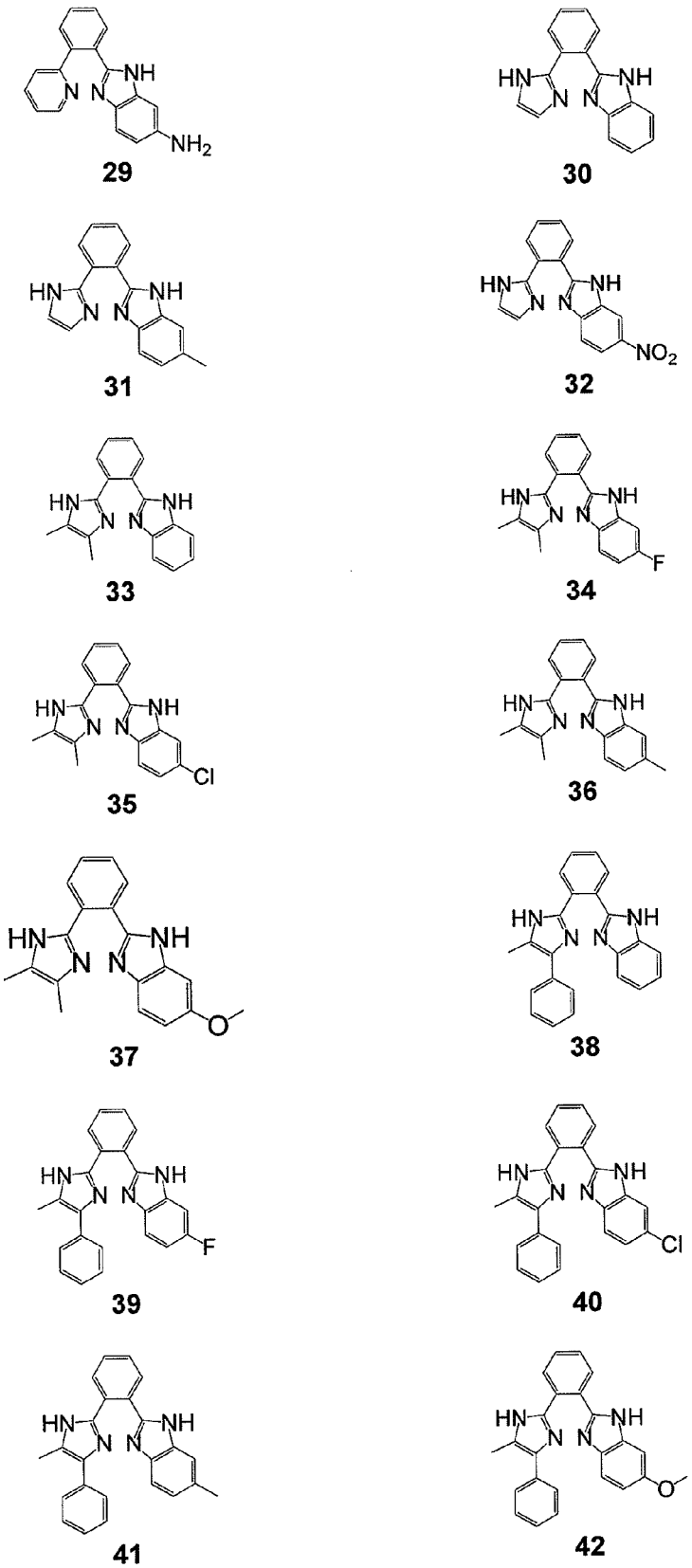
Figure 1D:
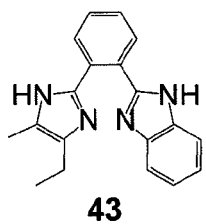
Figure 1D:
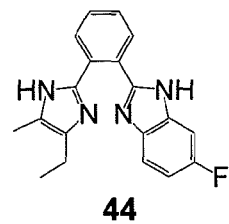
Figure 1D:
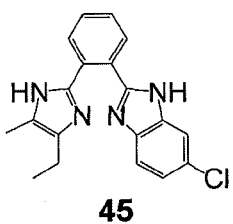
Figure 1D:
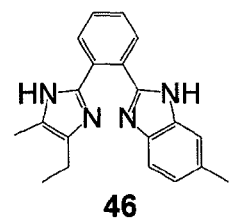
Figure 1D:
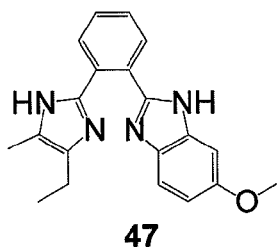
Figure 1D:
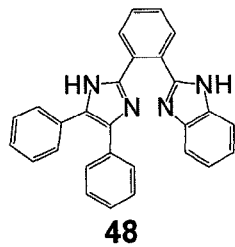
Figure 1D:
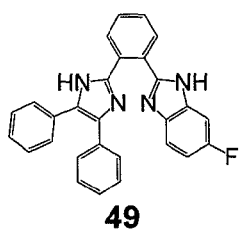
Figure 1D:
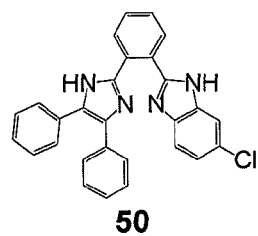
Figure 1D:
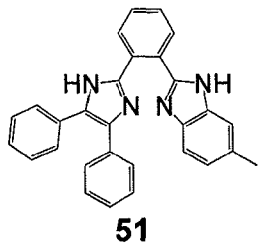
Figure 1D:
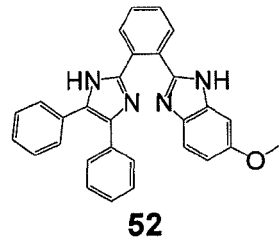
Figure 1D:
Figure 1D:
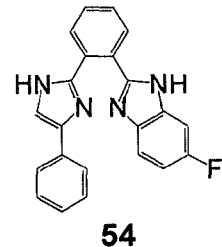
Figure 1E:
Figure 1E:
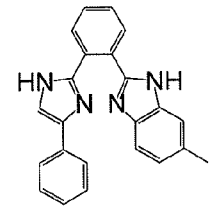
Figure 1E:
Figure 1E:
Figure 1E:
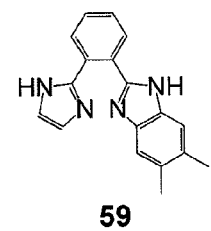
Figure 1E:
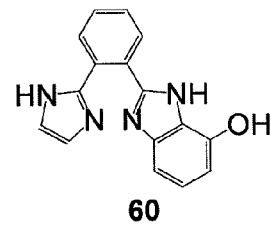
Figure 1E:
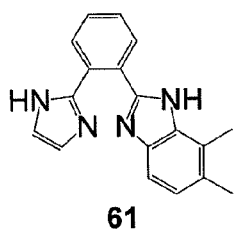
Figure 1E:
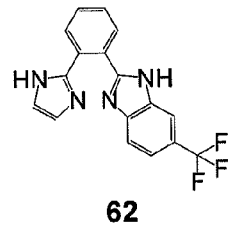
Figure 1E:
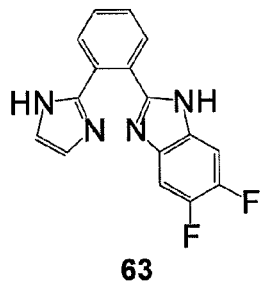
Figure 1E:
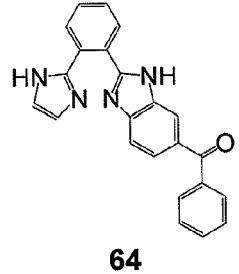
Figure 1E:
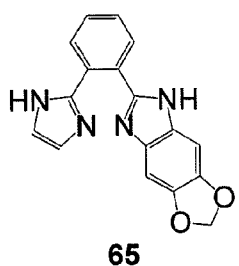
Figure 1E:
Figure 1F:
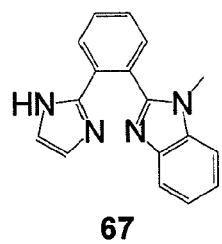
Figure 1F:
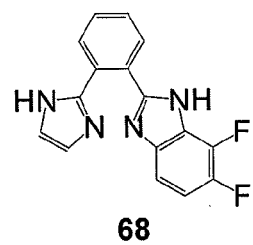
Figure 1F:
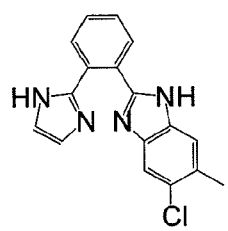
Figure 1F:
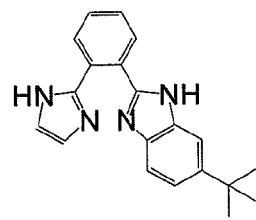
Figure 1F:
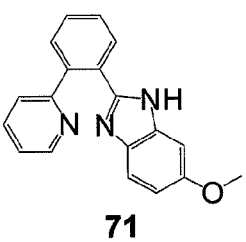
Figure 1F:
Figure 1F:
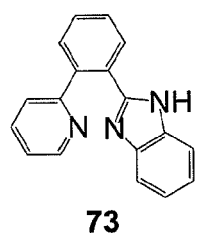
Figure 1F:
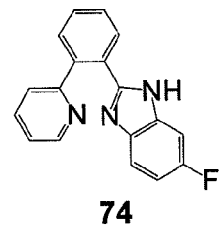
Figure 1F:
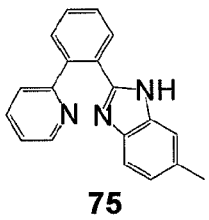
Figure 1F:
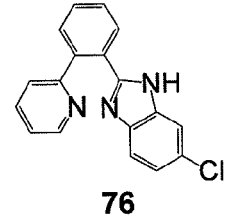
Figure 1F:
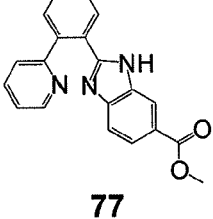
Figure 1F:
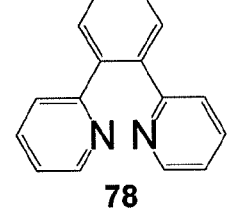
Figure 1G:
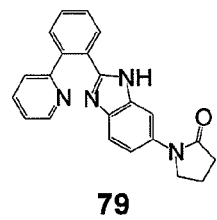
Figure 1G:
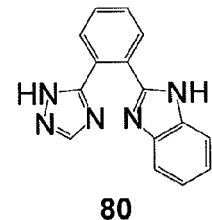
Figure 1G:
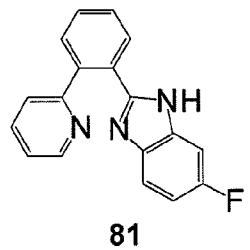
Figure 1G:
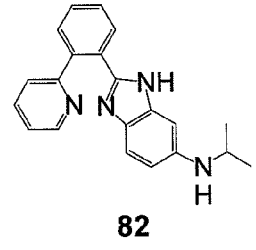
Figure 1G:
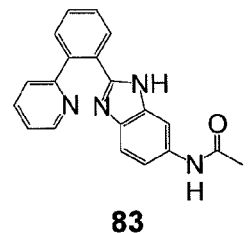
Figure 1G:
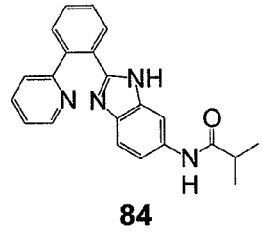
Figure 1G:
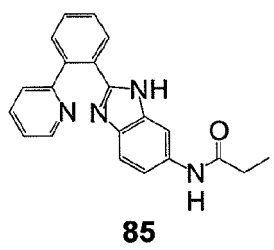
Figure 1G:
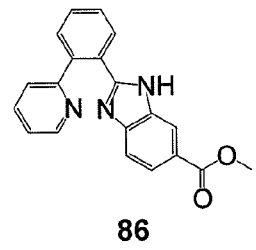
Figure 1G:
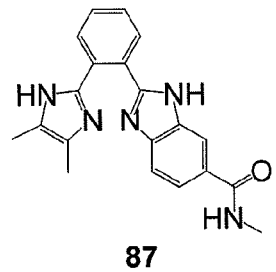
Figure 1G:
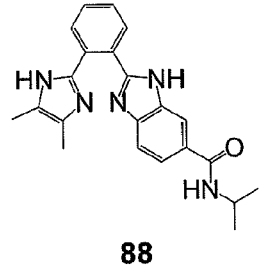
Figure 1G:
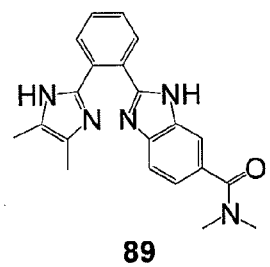
Figure 1G:
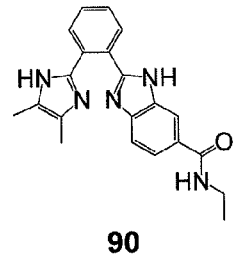
Figure 1H:
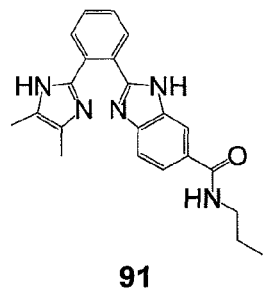
Figure 1H:
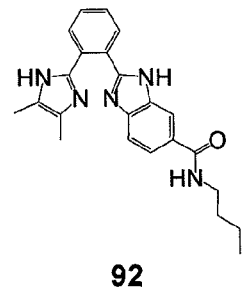
Figure 1H:
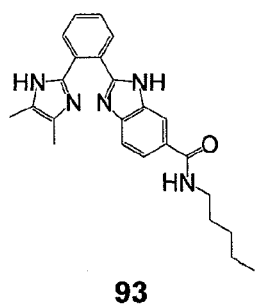
Figure 1H:
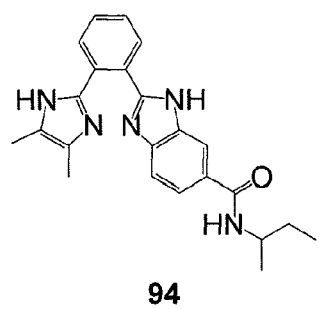
Figure 1H:
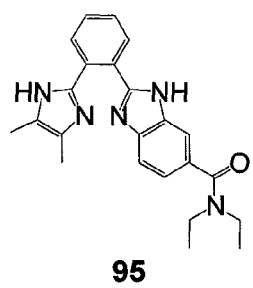
Figure 1H:
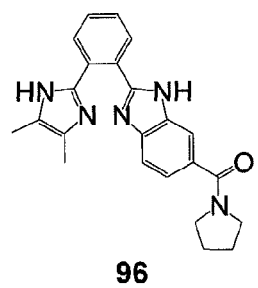
Figure 1H:
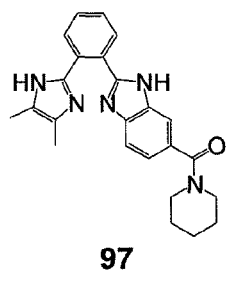
Figure 1H:
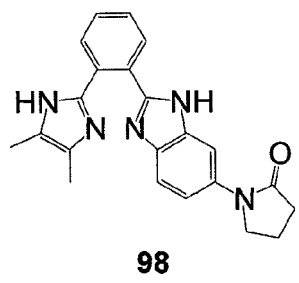
Figure 1H:
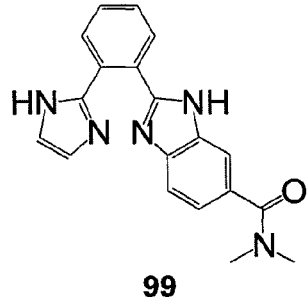
Figure 1H:
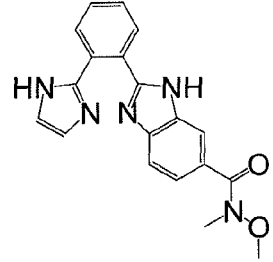
Figure 1I:
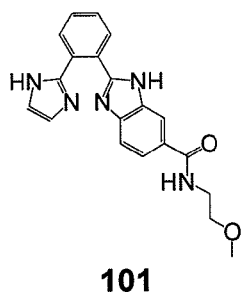
Figure 1I:
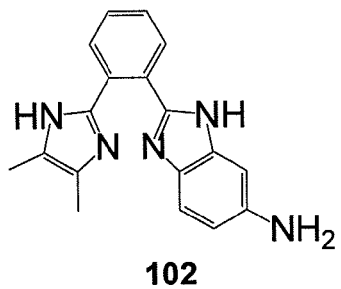
Figure 1I:
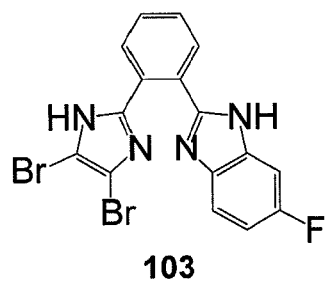
Figure 1I:
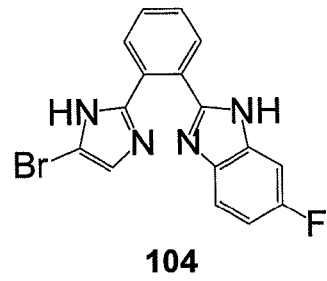
Figure 1I:
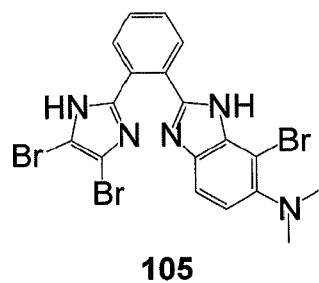
Figure 1I:
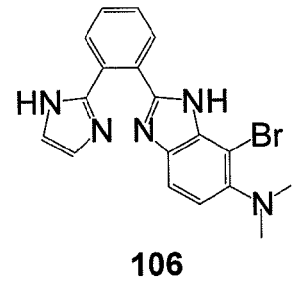
Figure 1I:
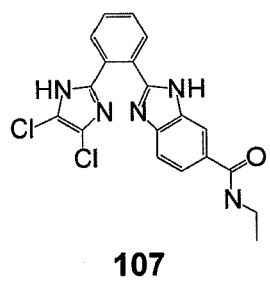
Figure 1I:
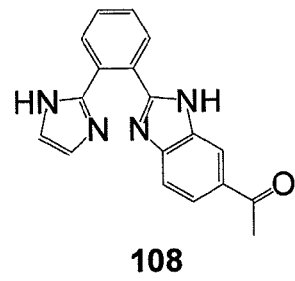
Figure 1I:
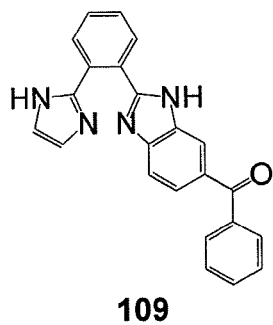
Figure 1I:
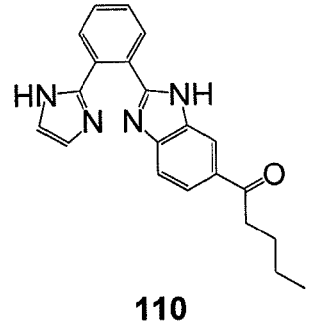
Figure 1J:
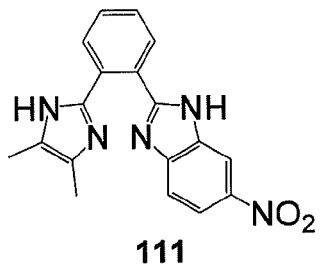
Figure 1J:
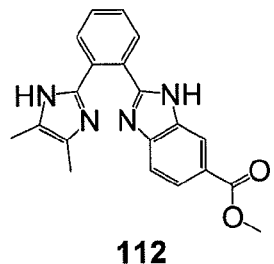
Figure 1J:
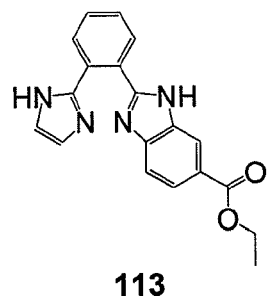
Figure 1J:
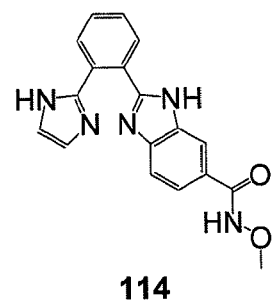
Figure 1J:
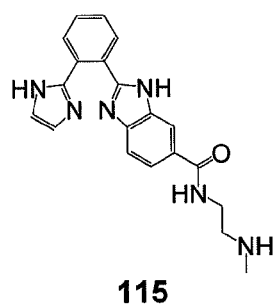
Figure 1J:
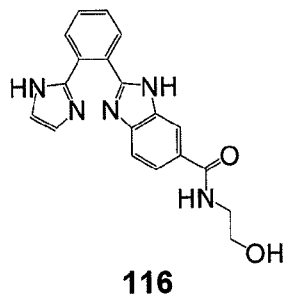
Figure 1J:
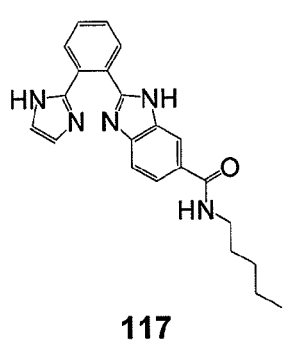
Figure 1J:
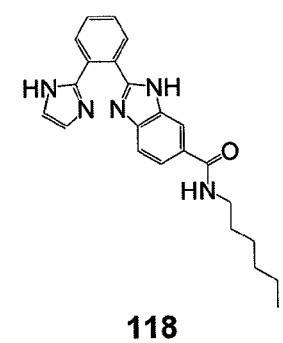
Figure 1J:
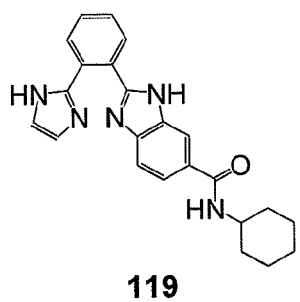
Figure 1J:
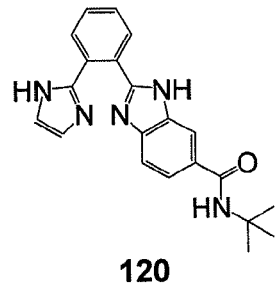
Figure 1K:
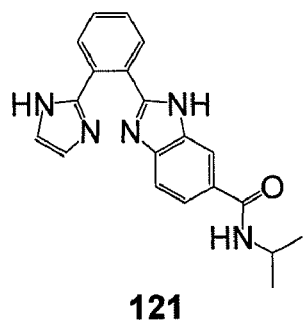
Figure 1K:
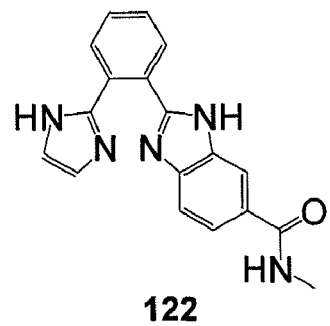
Figure 1K:
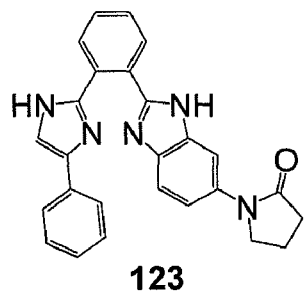
Figure 1K:
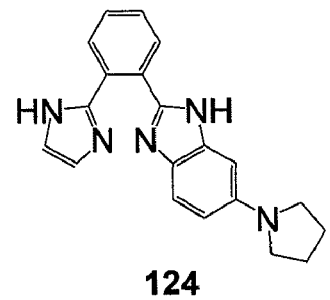
Figure 1K:
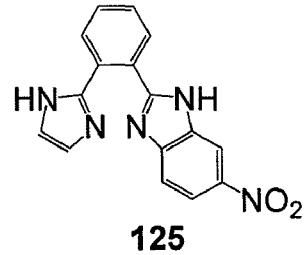

In an exemplary embodiment, the invention provides a compound having a structure according to FIG. 1.

Preparation of Asymmetrical Benzimidazoles

The following exemplary schemes illustrate methods of preparing the compounds of the invention. These methods are not limited to producing the compounds listed, but can be used to prepare other substrates as well. The compounds of the invention can also be produced by methods not explicitly illustrated in the schemes. The compounds can be prepared using readily available starting materials or known intermediates.

The following D substituents are offered to illustrate, but not to limit, the substituents of the claimed invention. In the following schemes, the substituents $D^1$-$D^{13}$ are independently selected from H, —OH, —$NH_2$, —$NO_2$, —$SO_2NH_2$, halogen, substituted or unsubstituted alkyl, substituted or unsubstituted heteroalkyl, substituted or unsubstituted 3- to 7-membered cycloalkyl, substituted or unsubstituted 5- to 7-membered heterocycloalkyl, substituted or unsubstituted aryl, and substituted or unsubstituted heteroaryl.

The non-benzimidazole substituents can be produced through the methods outlined in Scheme 1 or Scheme 2.

Scheme 1

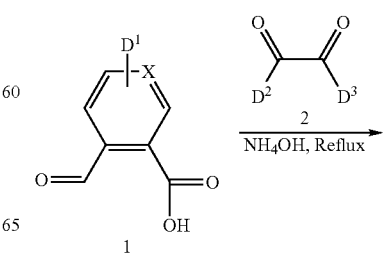

-continued

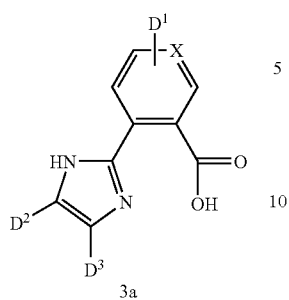

3a

In Scheme 1, compound 1 is reacted with an α-dicarbonyl compound 2 in the presence of ammonium hydroxide at reflux to produce the imidazole compound 3a.

Scheme 2

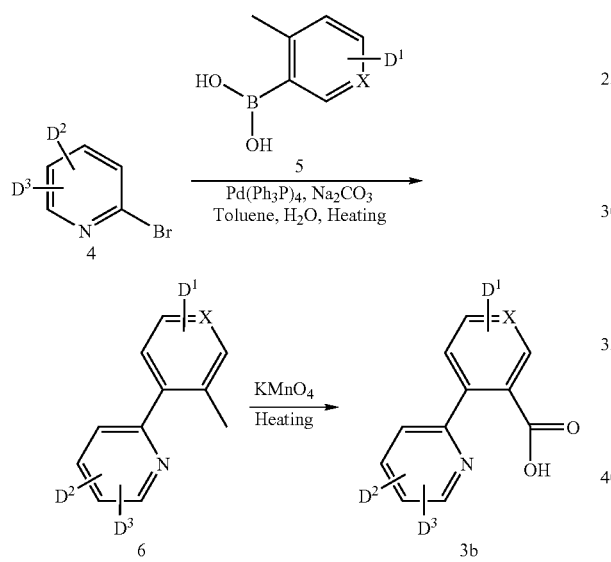

Alternatively, a bromo-substituted pyridine 4 is reacted with substituted boric acid 5 to produce compound 6. This compound is then oxidized with permanganate in order to produce pyridine compound 3b.

The benzimidazole substituent is added through the method outlined in Scheme 3.

Scheme 3

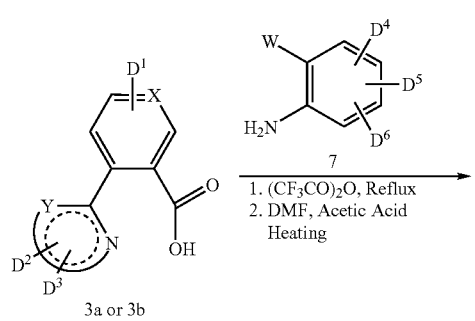

-continued

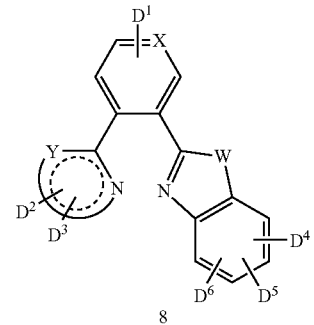

8

W = ND$^7$, O, S; Y = CH, ND$^7$, O, S; X = CH, N

In Scheme 3, compound 3a or 3b is reacted with compound 7 to produce asymmetric benzimidazole 8.

Amino-substituted asymmetric benzimidazoles are produced according to the method of Scheme 4.

Scheme 4

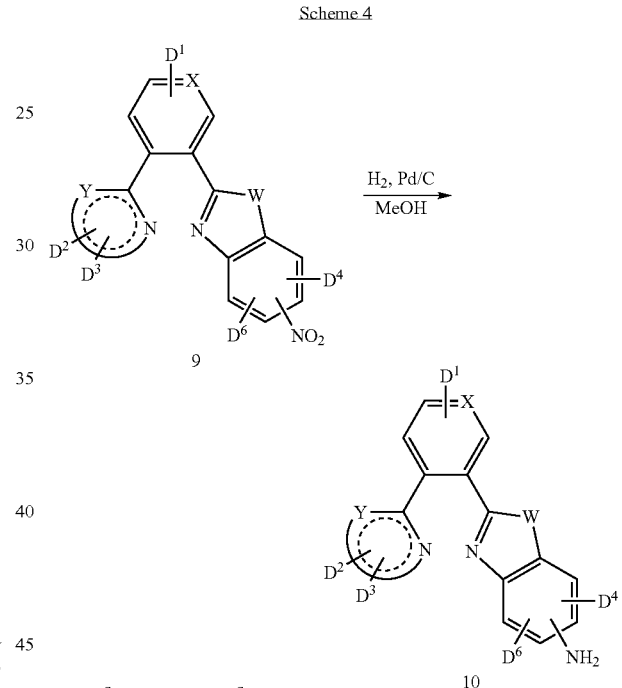

W = ND$^7$, O, S; Y = CH, ND$^7$, O, S; X = CH, N

In Scheme 4, the nitro adduct 9 is reduced to an amino adduct 10 through palladium catalyzed hydrogenation.

The amino group is substituted according to the method of Scheme 5.

Scheme 5

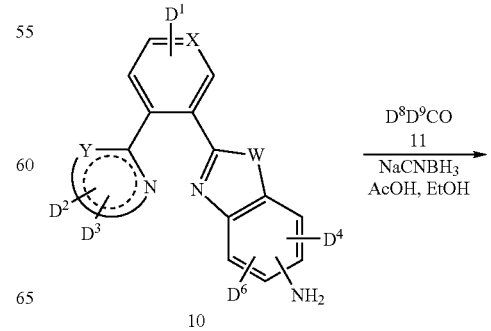

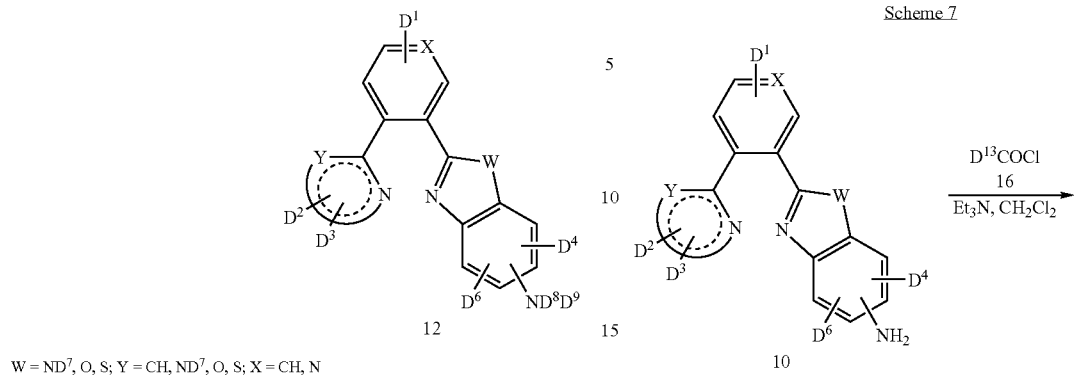

12

W = ND$^7$, O, S; Y = CH, ND$^7$, O, S; X = CH, N

In Scheme 5, compound 10 is reacted with compound 11 and sodium cyanoborohydride in acetic acid and ethanol in order to produce compound 12.

The ester-substituted asymmetric benzimidazole is converted to an amide-substituted asymmetric benzimidazole by the method of Scheme 6.

Scheme 6

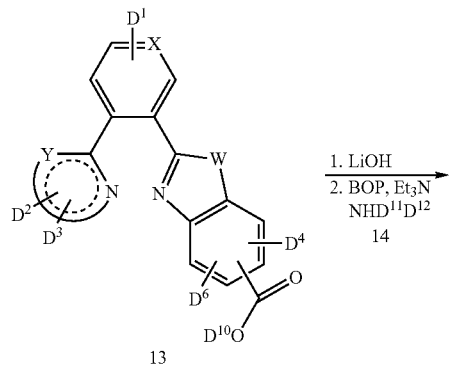

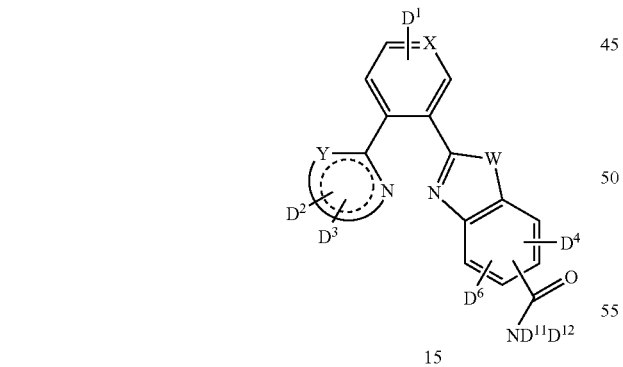

W = ND$^7$, O, S; Y = CH, ND$^7$, O, S; X = CH, N

In Scheme 6, compound 13 is first reacted with lithium hydroxide. Subsequently, BOP-reagent and compound 14 are added in order to produce compound 15.

The amino-substituted asymmetric benzimidazole is converted to an amide-substituted asymmetric benzimidazole by the method of Scheme 7.

Scheme 7

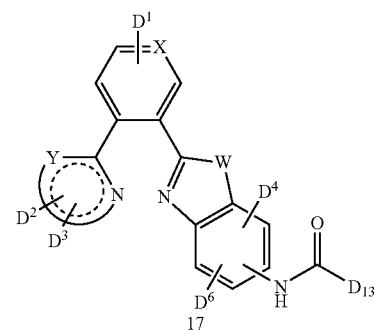

In Scheme 7, compound 10 is reacted with acyl chloride 16 in a mixture of triethylamine and dichloromethane in order to produce compound 17.

Compound 8 is halogenated according to the method of Scheme 8.

Scheme 8

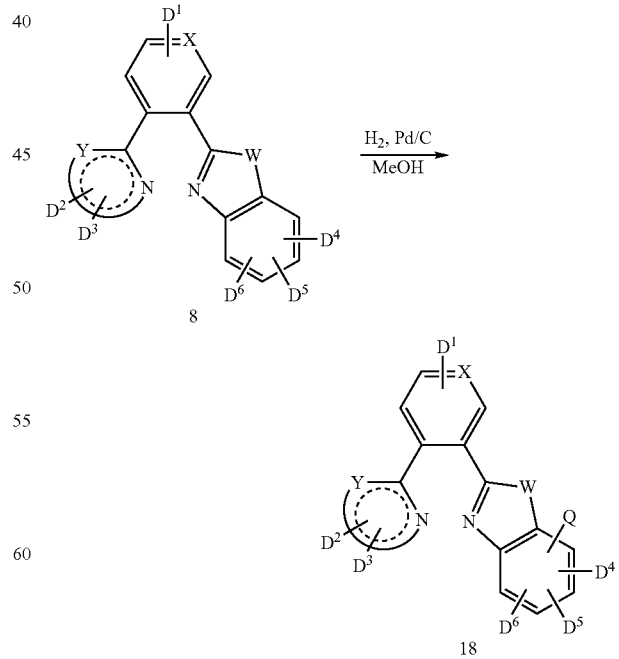

W = ND$^7$, O, S; Y = CH, ND$^7$, O, S; X = CH, N; Q = Cl, Br

In Scheme 8, compound 8 is reacted with either N-bromosuccinimide or N-chlorosuccinimide in DMF in order to produce halo-substituted compound 18.

Methods for preparing dimers, trimers and higher homologs of small organic molecules, such as those of the present invention, as well as methods of functionalizing a polyfunctional framework molecule are well known to those of skill in the art. For example, an aromatic amine of the invention is converted to the corresponding isothiocyanate by the action of thiophosgene. The resulting isothiocyanate is coupled to an amine of the invention, thereby forming either a homo- or heterodimeric species. Alternatively, the isothiocyanate is coupled with an amine-containing backbone, such as polylysine, thereby forming a conjugate between a polyvalent framework and a compound of the invention. If it is desired to prepare a heterofunctionalized polyvalent species, the polylysine is underlabeled with the first isothiocyanate and subsequently labeled with one or more different isothiocyanates. Alternatively, a mixture of isothiocyanates is added to the backbone. Purification proceeds by, for example, size exclusion chromatography, dialysis, nanofiltration and the like.

II. Assays for Modulators of Potassium Ion Channels

SK monomers as well as SK alleles and polymorphic variants are subunits of potassium channels. The activity of a potassium channel comprising SK subunits can be assessed using a variety of in vitro and in vivo assays, e.g., measuring current, measuring membrane potential, measuring ion flux, e.g., potassium or rubidium, measuring potassium concentration, measuring second messengers and transcription levels, using potassium-dependent yeast growth assays, and using e.g., voltage-sensitive dyes, radioactive tracers, and patch-clamp electrophysiology.

Furthermore, such assays can be used to test for inhibitors and activators of channels comprising SK. The SK family of channels is implicated in a number of disorders that are targets for a therapeutic or prophylactic regimen, which functions by blockade or inhibition of one or more members of the SK channel family. The compounds and methods of the invention are useful to treat central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as targets for neuroprotective agents (e.g., to prevent stroke and the like). The compounds of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

Modulators of the potassium channels are tested using biologically active SK, either recombinant or naturally occurring, or by using native cells, like cells from the nervous system expressing an SK channel. SK channels can be isolated, co-expressed or expressed in a cell, or expressed in a membrane derived from a cell. In such assays, SK is expressed alone to form a homomeric potassium channel or is co-expressed with a second subunit (e.g., another SK family member) so as to form a heteromeric potassium channel. Modulation is tested using one of the in vitro or in vivo assays described above. Samples or assays that are treated with a potential potassium channel inhibitor or activator are compared to control samples without the test compound, to examine the extent of modulation. Control samples (untreated with activators or inhibitors) are assigned a relative potassium channel activity value of 100. Inhibition of channels comprising SK is achieved when the potassium channel activity value relative to the control is less than 70%, preferably less than 40% and still more preferably, less than 30%. Compounds that decrease the flux of ions will cause a detectable decrease in the ion current density by decreasing the probability of a channel comprising SK being open, by decreasing conductance through the channel, and decreasing the number or expression of channels.

Changes in ion flux may be assessed by determining changes in polarization (i.e., electrical potential) of the cell or membrane expressing the potassium channel. A preferred means to determine changes in cellular polarization is by measuring changes in current or voltage with the voltage-clamp and patch-clamp techniques, using the "cell-attached" mode, the "inside-out" mode, the "outside-out" mode, the "perforated cell" mode, the "one or two electrode" mode, or the "whole cell" mode (see, e.g., Ackerman et al., *New Engl. J. Med.* 336: 1575-1595 (1997)). Whole cell currents are conveniently determined using the standard methodology (see, e.g., Hamil et al., *Pflugers. Archiv.* 391: 85 (1981)). Other known assays include: radiolabeled rubidium flux assays and fluorescence assays using voltage-sensitive dyes (see, e.g., Vestergarrd-Bogind et al., *J. Membrane Biol.* 88: 67-75 (1988); Daniel et al., *J. Pharmacol. Meth.* 25: 185-193 (1991); Holevinsky et al., *J. Membrane Biology* 137: 59-70 (1994)). Assays for compounds capable of inhibiting or increasing potassium flux through the channel proteins can be performed by application of the compounds to a bath solution in contact with and comprising cells having a channel of the present invention (see, e.g., Blatz et al., *Nature* 323: 718-720 (1986); Park, *J. Physiol.* 481: 555-570 (1994)). Generally, the compounds to be tested are present in the range from about 1 pM to about 100 mM, preferably from about 1 pM to about 1 µM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin-binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides.

III. Pharmaceutical Compositions of Potassium Channel Modulators

In another aspect, the present invention provides pharmaceutical compositions comprising a pharmaceutically acceptable excipient and a compound of Formula I provided above.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of Formula I, or a pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

IV. Methods for Modulating Ion Flow in Voltage-Dependent Potassium Channels

In yet another aspect, the present invention provides methods for modulating ion flow through voltage dependent potassium channels in a cell, comprising contacting a cell containing the target ion channels with a potassium channel-modulating amount of a compound of Formula I provided above.

The methods provided in this aspect of the invention are useful for the diagnosis of conditions that can be treated by modulating ion flux through voltage-dependent potassium channels, or for determining if a patient will be responsive to therapeutic agents, which act by modulating potassium channels. In particular, a patient's cell sample can be obtained and contacted with a compound of Formula I above and the ion flux can be measured relative to a cell's ion flux in the absence of a compound of Formula I. A decrease in ion flux will typically indicate that the patient will be responsive to a therapeutic regimen of ion channel blockers.

V. Methods for Treating Conditions Mediated by Voltage-Dependent Potassium Channels In still another aspect, the present invention provides a method for the treatment of a disorder or condition through modulation of a voltage-dependent potassium channel. In this method, a subject in need of such treatment is administered an effective amount of a compound of Formula I provided above. In a preferred embodiment, the compounds provided herein are used to treat a disorder or condition by modulating an ion channel of the hSK family.

The compounds provided herein are useful as potassium channel modulators and find therapeutic utility via modulation of voltage-dependent potassium channels in the treatment of diseases or conditions. The potassium channels that are typically modulated are described herein as voltage-dependent potassium channels such as the hSK potassium channels. As noted above, these channels may hSK1, hSK2, hSK3 and other members of the hSK family of ion channels.

The conditions that can be treated with the compounds and compositions of the present invention may include, but are not limited to, central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as active as neuroprotective agents (e.g., to prevent stroke and the like). The compounds of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

In treatment of the above conditions, the compounds utilized in the method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

EXAMPLES

General

In the examples below, unless otherwise stated, temperatures are given in degrees Celsius (° C.); operations were carried out at room or ambient temperature, "rt," or "RT," (typically a range of from about 18-25° C.); evaporation of solvent was carried out using a rotary evaporator under reduced pressure (typically, 4.5-30 mm Hg) with a bath temperature of up to 60° C.; the course of reactions was typically followed by thin layer chromatography (TLC) and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours). The compounds of the invention were generally isolated in yields of from about 30% to about 90% using the methods set forth hereinbelow.

Unless otherwise specified, all solvents (HPLC grade) and reagents were purchased from suppliers and used without further purification. Reactions were conducted under a blanket of argon unless otherwise stated. Analytical TLC was performed on Whatman Inc. 60 silica gel plates (0.25 mm thickness). Compounds were visualized under a UV lamp (254 nM) or by developing with KMnO$_4$/KOH, ninhydrin or Hanessian's solution. Flash chromatography was done using silica gel from Selectro Scientific (particle size 32-63). $^1$H NMR, $^{19}$F NMR and $^{13}$C NMR spectra were recorded on a Varian 300 machine at 300 MHz, 282 MHz and 75.7 MHz, respectively. Melting points were recorded on a Electrothermal IA9100 apparatus and were uncorrected.

Example 1

Synthesis of 3a
  1.1 General Method
  A mixture of 0.5 mol of 1 and 0.55 mol of 2 in 400 mL of concentrated ammonium hydroxide was heated overnight at 80° C. After removal of excess ammonium hydroxide water under reduced pressure, the crude yellow solid was triturated with ethyl acetate to give 0.45 mol of the desired product 3a.
  1.2 Results
  Analytical data for exemplary compounds of structure 3a are provided below.
    1.2.a 2-(1H-Imidazol-2-yl)-benzoic Acid
    $^1$H NMR (300 MHz, DMSO-d$_6$) δ 7.90 (d, J=7.7 Hz, 1H), 7.80 (d, J=7.7 Hz, 1H), 7.60 (t, J=7.1 Hz, 1H), 7.48 (t, J=7.3 Hz, 1H), 7.26 (s, 2H); MS m/z: 189 (M+H).
    1.2.b 2-(5-Phenyl-1H-imidazol-2-yl)-benzoic Acid
    $^1$H NMR (300 MHz, DMSO-d$_6$) δ 8.00 (d, J=7.6 Hz, 1H), 7.83 (d, J=8.4 Hz, 1H), 7.77 (d, J=7.3 Hz, 2H), 7.69 (s, 1H), 7.51 (t, J=7.3 Hz, 1H), 7.45-7.33 (m, 3H), 7.21 (t, J=7.3 Hz, 1H); MS m/z: 265 (M+H).
    1.2.c 2-(4-Methyl-5-phenyl-1H-imidazol-2-yl)-benzoic Acid
    $^1$H NMR (300 MHz, DMSO-d$_6$) δ 7.96 (d, J=7.8 Hz, 1H), 7.88 (d, J=7.5 Hz, 1H), 7.65-7.59 (m, 3H), 7.56-7.39 (m, 3H), 7.27 (t, J=7.4 Hz, 1H), 2.46 (s, 3H); MS m/z: 279 (M+H).

Example 2

Synthesis of 3b
  2.1 General Method
  A mixture of 58.8 mmol of 4, 58.8 mmol of 5, 5.2 mmol of Pd(PPh$_3$)$_4$, and 117.7 mmol of Na$_2$CO$_3$ in 100 mL of toluene, and 100 mL of water was refluxed overnight under N$_2$. The reaction mixture was diluted with 300 mL of ethyl acetate and the two layers were separated. The organic phase was washed with saturated NaCl, dried over MgSO$_4$, and concentrated under reduced pressure. The residue was purified by column chromatography on silica gel to give 47 mmol of 6.
  A mixture of 53 mmol of 6 and 211 mmol of KMnO$_4$ in 200 mL of water was refluxed for 2 days. The mixture was diluted with 100 mL of methanol and filtered through celite. The colorless solution was collected and concentrated in vacuo to afford a quantitative yield of 3b.
  2.2 Results
  Analytical data for an exemplary compound of structure 3b is provided below.
    2.2.a 2-Pyridin-2-yl-benzoic Acid
    $^1$H NMR (300 MHz, DMSO-d$_6$) δ 8.56 (d, J=4.5 Hz, 1H), 7.84 (dt, J$_1$=7.8 Hz, J$_2$=1.7 Hz, 1H), 7.68 (t, J=7.4 Hz, 1H), 7.61-7.53 (m, 3H), 7.51-7.35 (m, 1H), 7.33 (t, J=4.8 Hz, 1H); MS m/z: 200 (M+H).

Example 3

Synthesis of 8
  3.1 General Method
  A suspension of 15.9 mmol of the benzoic acid 3a or 3b in 20 mL of trifluoroacetic anhydride was refluxed for one hour before trifluroacetic anhydride was removed under reduced pressure. To the residue dissolved in 100 mL of DMF was added 15.9 mmol of 7 and the resulting solution was stirred at 140° C. for one hour before 20 mL of acetic acid was added. After the mixture was refluxed for three hours, the solvents were removed under reduced pressure. The residue was purified either by crystallization or column chromatography on silica gel to give 8.2 mmol of 8.

3.2 Results

Analytical data for exemplary compounds of structure 8 are provided below.

3.2.a 2-[2-(1H-Imidazol-2-yl)-phenyl]-5-nitro-1H-benzimidazole $^1$H NMR (300 MHz, DMSO-$d_6$) δ 8.34 (s, 1H), 8.23 (d, J=7.9 Hz, 1H), 8.12 (d, J=8.9 Hz, 1H), 7.92-7.86 (m, 2H), 7.81 (d, J=7.3 Hz, 1H), 7.76 (s, 2H), 7.70 (d, J=8.8 Hz, 1H); MS m/z: 306 (M+H).

3.2.b 1-{2-[2-(5-Phenyl-1H-imidazol-2-yl)-phenyl]-1H-benzimidazol-5-yl}-pyrrolidin-2-one $^1$H NMR (300 MHz, DMSO-$d_6$) δ 8.16-8.04 (m, 2H), 7.77 (d, J=7.3 Hz, 2H), 7.79-7.76 (m, 1H), 7.62-7.57 (m, 4H), 7.45-7.35 (m, 3H), 7.25-7.23 (m, 1H), 3.91 (t, J=7.0 Hz, 2H), 2.54-2.48 (m, 2H), 2.10-2.06 (m, 2H); MS m/z: 420 (M+H).

3.2.c 1-{2-[2-(1H-Imidazol-2-yl)-phenyl]-1H-benzimidazol-5-yl}-pyrrolidin-2-one $^1$H NMR (300 MHz, DMSO-$d_6$) δ 8.12 (d, J=7.3 Hz, 1H), 7.96 (d, J=7.3 Hz, 1H), 7.88 (s, 1H), 7.61-7.47 (m, 4H), 7.23 (s, 2H), 3.90 (t, J=7.0 Hz, 2H), 2.53-2.48 (m, 2H), 2.08 (t, J=7.2 Hz, 2H); MS m/z: 344 (M+H).

3.2.d 2-[2-(4,5-Dimethyl-1H-imidazol-2-yl)-phenyl]-5-fluoro-1H-benzimidazole $^1$H NMR (300 MHz, DMSO-$d_6$) δ 12.4 (bs, 2H), 8.37 (dd, $J_1$=7.5 Hz, $J_2$=1.5 Hz, 1H), 7.86 (dd, $J_1$=7.8 Hz, $J_2$=1.4 Hz, 1H), 7.67-7.45 (m, 4H), 7.05 (dt, $J_1$=9.7 Hz, $J_2$=2.4 Hz, 1H), 2.19 (s, 6H); MS m/z: 307 (M+H).

3.2.e 6-[2-(1H-Imidazol-2-yl)-phenyl]-5H-[1,3]dioxolo[4',5':4,5]benz[1,2-d]imidazole $^1$H NMR (300 MHz, DMSO-$d_6$) δ 13.70 (bs, 2H), 8.12 (dd, $J_1$=6.7 Hz, $J_2$=2.4 Hz, 1H), 7.97 (dd, $J_1$=6.8 Hz, $J_2$=2.4 Hz, 1H), 7.54-7.50 (m, 2H), 7.23 (s, 2H), 7.16 (s, 2H), 6.00 (s, 2H); MS m/z: 305 (M+H).

3.2.f 6-Chloro-2-[2-(4,5-diphenyl-1H-imidazol-2-yl)-phenyl]-1H-benzimidazole $^1$H NMR (300 MHz, DMSO-$d_6$) δ 13.90 (bs, 2H), 8.23 (d, J=7.7 Hz, 1H), 8.10 (d, J=7.3 Hz, 1H), 7.68-7.56 (m, 4H), 7.47-7.37 (m, 4H), 7.35-7.25 (m, 7H); MS m/z: 447 (M+H).

3.2.g 6-Fluoro-2-(2-pyridin-2-yl-phenyl)-1H-benzimidazole $^1$H NMR (300 MHz, CD$_3$OD) δ 8.46 (d, J=4.3 Hz, 1H), 7.79 (t, J=6.0 Hz, 1H), 7.69 (t, J=5.6 Hz, 1H), 7.66-7.61 (m, 3H), 7.46-7.37 (m, 2H), 7.31-7.24 (m, 2H), 7.15 (t, J=9.0 Hz, 1H), 7.00 (t, J=7.3 Hz, 1H); MS m/z: 290 (M+H).

Example 4

Synthesis of 10

4.1 General Method

A solution or a suspension of 8.2 mmol of 9 and 0.5 g of Pd/C (10%) in 150 mL of methanol was stirred overnight under H$_2$ (1 atm). After filtering through celite, the solution was concentrated under a reduced pressure to give 8.2 mmol of 10.

4.2 Results

Analytical data for exemplary compounds of structure 10 are provided below.

4.2.a 2-[2-(1H-Imidazol-2-yl)-phenyl]-3H-benzimidazol-5-ylamine $^1$H NMR (300 MHz, DMSO-$d_6$) δ 8.00 (dd, $J_1$=5.7 Hz, $J_2$=3.3 Hz, 2H), 7.61 (dd, $J_1$=5.8 Hz, $J_2$=3.3 Hz, 2H), 7.35 (s, 2H), 7.32 (d, J=8.7 Hz, 1H), 6.70 (d, J=2.0 Hz, 1H), 6.61 (dd, $J_1$=8.5 Hz, $J_2$=2.0 Hz, 1H), 3.15 (s, 2H); MS m/z: 276 (M+H).

4.2.b 2-[2-(4,5-Dihydro-oxazol-2-yl)-phenyl]-3H-benzimidazol-5-ylamine $^1$H NMR (300 MHz, CD$_3$OD) δ 7.87 (d, J=7.6 Hz, 1H), 7.80 (d, J=7.1 Hz, 1H), 7.64 (dd, $J_1$=7.5 Hz, $J_2$=6.5 Hz, 1H), 7.57 (dd, $J_1$=7.5 Hz, $J_2$=6.5 Hz, 1H), 7.37 (d, J=8.5 Hz, 1H), 6.91 (d, J=1.7 Hz, 1H), 7.76 (dd, $J_1$=8.7 Hz, $J_2$=2.1 Hz, 1H), 4.28 (t, J=9.7 Hz, 2H), 3.96 (t, J=9.4 Hz, 2H); MS m/z: 279 (M+H).

4.2.c 2-[2-(4,5-Dihydro-1H-imidazol-2-yl)-phenyl]-3H-benzimidazol-5-ylamine $^1$H NMR (300 MHz, CD$_3$OD) δ 7.87 (d, J=7.7 Hz, 1H), 7.68 (d, J=8.7 Hz, 1H), 7.64-7.55 (m, 3H), 7.38 (d, J=8.6 Hz, 1H), 6.93 (s, 1H), 6.77 (d, J=8.7 Hz, 1H), 3.70 (s, 4H), 3.34 (s, 2H); MS m/z: 278 (M+H).

4.2.d 2-(2-Pyridin-2-yl-phenyl)-3H-benzimidazol-5-ylamine $^1$H NMR (300 MHz, CD$_3$OD) δ 8.47 (d, J=3.9 Hz, 1H), 7.76 (t, J=8.3 Hz, 2H), 7.70-7.60 (m, 3H), 7.31-7.32 (m, 3H), 6.79 (s, 1H), 6.73 (d, J=8.7 Hz, 1H), 3.30 (s, 2H); MS m/z: 287 (M+H).

Example 5

Synthesis of 12

5.1 General Method

Sodium cyanoborohydride (3.5 mmol) was added to a solution of 0.69 mmol of 10 and 3.5 mmol of 11 in 20 mL of ethanol and 5 mL of acetic acid. The solution was stirred for two hours before all solvents were removed under vacuum. The residue was dissolved in ethyl acetate and the organic solution was washed with water. The organic layer was dried with magnesium sulfate. The crude product was concentrated in vacuo and purified by column chromatography on silica gel to give 0.35 mmol of 12.

5.2 Results

Analytical data for exemplary compounds of structure 12 are provided below.

5.2.a {2-[2-(1H-Imidazol-2-yl)-phenyl]-3H-benzimidazol-5-yl}-dimethyl-amine $^1$H NMR (300 MHz, DMSO-$d_6$) δ 8.21 (d, J=7.5 Hz, 1H), 7.93-7.83 (m, 4H), 7.75 (s, 2H), 7.75-7.71 (m, 2H), 3.12 (s, 6H); MS m/z: 304 (M+H).

5.2.b Isopropyl-[2-(2-pyridin-2-yl-phenyl)-3H-benzimidazol-5-yl]-amine $^1$H NMR (300 MHz, DMSO-$d_6$) δ 8.46 (bs, 1H), 8.22 (d, J=4.5 Hz, 1H), 7.89 (d, J=7.7 Hz, 1H), 7.74-7.65 (m, 2H), 7.64-7.61 (m, 3H), 7.46 (d, J=7.5 Hz, 1H), 7.35 (d, J=8.9 Hz, 1H), 7.30-7.20 (m, 1H), 3.60-3.50 (m, 1H), 1.15 (s, 3H), 1.14 (s, 3H); MS m/z: 329 (M+H).

Example 6

Synthesis of 15

6.1 General Method

A mixture of 3.05 mmol of 13 and 15.2 mmol of lithium hydroxide in 50 mL of ethanol and 10 mL of water was refluxed for 2 days. After removal of solvents, the residue was dissolved in 20 mL of water and the aqueous solution was acidified with 10% hydrochloric acid. The aqueous solution was extracted with ethyl acetate and the combined organic phase was concentrated in vacuo to give crude acid product.

A solution of 3.29 mmol of the crude acid above, 4.58 mL of triethylamine, 1.75 g of BOP-reagent, and 3.29 mmol of 14 in 150 mL of THF was stirred for three days. The reaction mixture was concentrated in vacuo, and the residue was dissolved in 200 mL of ethyl acetate. The organic solution was washed with saturated NH$_4$Cl, dried over MgSO$_4$, and concentrated in vacuo. The crude product was purified by column chromatography on silica gel to give 0.5 mmol of 15.

6.2 Results

Analytical data for an exemplary compound of structure 15 is provided below.

6.2. a 2-[2-(4,5-Dimethyl-1H-imidazol-2-yl)-phenyl]-3H-benzimidazole-5-carboxylic acid methylamide $^1$H NMR (300 MHz, CD$_3$OD) δ 13.77 (bs, 2H), 8.47 (d, J=4.7 Hz, 1H), 8.13 (d, J=7.7 Hz, 1H), 8.03 (s, 1H), 7.87 (dt, J=7.5 Hz, J$_2$=1.9 Hz, 1H), 7.80-7.74 (m, 2H), 7.57 (d, J=8.5 Hz, 1H), 2.80 (s, 3H), 2.78 (s, 3H), 2.22 (s, 3H); MS m/z: 346 (M+H).

Example 7

Synthesis of 17

7.1 General Method

A solution of 0.59 mmol of 10, 0.1 mL triethylamine, and 0.29 mmol of 16 in 3 mL of dichloromethane was stirred for 24 hrs. Then dichloromethane and excess acid chloride were removed under a vacuum. The residue was dissolved in 3 mL of methanol followed by the addition of 0.0010 g of NaHCO$_3$. The resulting suspension was stirred for four hours before the solvent was removed in vacuo. The crude product was purified by column chromatography on silica gel to give 0.22 mmol of 17.

7.2 Results

Analytical data for exemplary compounds of structure 17 are provided below.

7.2.a N-[2-(2-Pyridin-2-yl-phenyl)-3H-benzimidazol-5-yl]-propionamide $^1$H NMR (300 MHz, DMSO-d$_6$) δ 12.12 (bs, 1H), 9.83 (s, 1H), 8.50 (d, J=4.5 Hz, 1H), 7.94 (s, 1H), 7.73 (t, J=7.0 Hz, 2H), 7.64-7.57 (m, 3H), 7.40 (d, J=8.8 Hz, 1H), 7.25-7.21 (m, 1H), 7.10 (d, J=7.7 Hz, 1H), 2.42 (s, 1H), 2.29 (dt, J$_1$=6.9 Hz, J$_2$=7.7 Hz, 1H), 1.07 (t, J=7.7 Hz, 3H); MS m/z: 343 (M+H).

7.2. b N-[2-(2-Pyridin-2-yl-phenyl)-3H-benzimidazol-5-yl]-isobutyramide $^1$H NMR (300 MHz, DMSO-d$_6$) δ 12.12 (bs, 1H), 9.80 (s, 1H), 8.50 (d, J=4.0 Hz, 1H), 7.94 (s, 1H), 7.75-7.21 (m, 2H), 7.64-7.54 (m, 3H), 7.41 (d, J=8.7 Hz, 1H), 7.34-7.21 (m, 1H), 7.10 (t, J=7.9 Hz, 1H), 2.59-2.53 (m, 1H), 1.09 (s, 3H), 1.05 (s, 3H); MS m/z: 357 (M+H).

Example 8

Synthesis of 18

8.1 General Method

A mixture of 0.1 mmol of 8 and 0.15 mmol of N-bromosuccinimide or N-chlorosuccinimide in 5 mL of DMF was stirred at room temperature overnight. After evaporation of the solvent under reduced pressure, the crude product was purified by column chromatography on silica gel to give 0.06 mmol of 18.

8.2 Results

Analytical data for exemplary compounds of structure 18 are provided below.

8.2. a 2-[2-(5-Bromo-1H-imidazol-2-yl)-phenyl]-6-fluoro-1H-benzimidazole $^1$H NMR (300 MHz, CD$_3$OD) δ 7.87-7.85 (m, 2H), 7.64-7.53 (m, 3H), 7.27 (dd, J$_1$=9.1 Hz, J$_2$=2.3 Hz, 1H), 7.16 (s, 1H), 7.04 (dt, J$_1$=9.6 Hz, J$_2$=2.3 Hz, 1H); MS m/z: 357 (M+H).

8.2. b 2-[2-(4,5-Dibromo-1H-imidazol-2-yl)-phenyl]-6-fluoro-1H-benzimidazole $^1$H NMR (300 MHz, CD$_3$OD) δ 7.87-7.82 (m, 2H), 7.62-7.53 (m, 3H), 7.26 (dd, J$_1$=9.1 Hz, J$_2$=2.2 Hz, 1H), 7.05 (dt, J$_1$=9.1 Hz, J$_2$=2.4 Hz, 1H); MS m/z: 435 (M+H).

8.2. c {2-[2-(4,5-Dibromo-1H-imidazol-2-yl)-phenyl]-3H-benzimidazol-5-yl}-dimethyl-amine $^1$H NMR (300 MHz, CD$_3$OD) δ 8.04-7.98 (m, 2H), 7.63-7.59 (m, 2H), 7.51 (d, J=8.7 Hz, 1H), 7.23 (d, J=8.7 Hz, 1H), 2.82 (s, 6H); MS m/z: 460 (M+H).

Example 9

Assay for Compound Activity Towards hSK Channels

Cells expressing small conductance, calcium activated potassium channels, such as SK-like channels, were loaded with $^{86}$Rb$^+$ by culture in media containing $^{86}$RbCl. Following loading, the culture media was removed and the cells were washed in EBSS to remove residual traces of $^{86}$Rb$^+$. Cells were preincubated with drug (0.01-30 μM in EBSS) and then $^{86}$Rb$^+$ efflux was stimulated by exposing cells to EBSS solution supplemented with a calcium ionophore, such as ionomycin, in the continued presence of the drug. After a suitable efflux period, the EBSS/ionophore solution was removed from the cells and the $^{86}$Rb$^+$ content was determined by Cherenkov counting (Wallac Trilux). Cells were then lysed with a SDS solution and the $^{86}$Rb$^+$ content of the lysate was determined. Percent $^{86}$Rb$^+$ efflux was calculated according to Equation 1:

$$(^{86}Rb^+ \text{content in } EBSS/(^{86}Rb^+\text{content in } EBSS+^{86}Rb^+ \text{content of the lysate}))\times 100 \qquad (1)$$

What is claimed is:

1. A compound of Formula I:

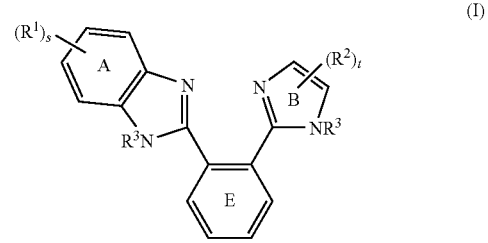

(I)

wherein
s is an integer from 1 to 4;
t is an integer from 1 to 2;
R$^1$ and R$^2$ are members independently selected from H, OR$^7$, NR$^8$R$^9$, NO$_2$, SO$_2$NR$^8$R$^9$, halogen, unsubstituted alkyl, substituted or unsubstituted heteroalkyl, unsubstituted 3- to 7-membered cycloalkyl, unsubstituted 5- to 7-membered heterocycloalkyl, unsubstituted aryl, unsubstituted heteroaryl, carboxyl, C(O)NH$_2$, alkyl amides, aryl amides, sulfonamides, thioureas, esters, carbamate, ether, hydroxy substituted alkyl or ketone;
wherein R$^7$, R$^8$, and R$^9$ are independently selected from hydrogen, unsubstituted alkyl, unsubstituted heteroalkyl, unsubstituted 3- to 7-membered cycloalkyl, unsubstituted 5- to 7-membered heterocycloalkyl, unsubstituted aryl, and unsubstituted heteroaryl;
or wherein R$^8$ and R$^9$ are taken together with the atoms to which they are joined to form a substituted or unsubstituted 5- to 7-membered ring;
two R$^1$ groups together with the atoms to which they are joined form an unsubstituted 5- to 7-membered ring; or
wherein if the A ring is substituted with more than one R$^1$, then each R$^1$ is optionally different;
wherein if the B ring is substituted with more than one R$^2$, then each R$^2$ is optionally different;

wherein each R³ is independently selected from the group consisting of H, and substituted or unsubstituted alkyl; and the pharmaceutically acceptable salts of the compound.

2. The compound according to claim 1, wherein the A phenyl ring is substituted with a member selected from the group consisting of NH₂, alkyl amines, arylamine, carboxyl, esters, C(O)NH₂, alkyl amides, aryl amides, sulfonamides, thioureas, halogens, alkoxy, carbamate, ether and hydroxy.

3. The compound according to claim 1, of Formula V:

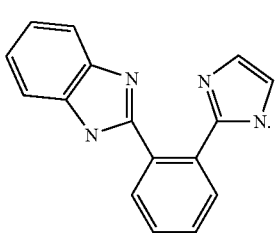

(V)

4. A composition comprising a pharmaceutically acceptable excipient and a compound of claim 1.

5. A composition comprising a pharmaceutically acceptable excipient and a compound of claim 2.

6. The composition according to claim 4 comprising a compound of Formula V:

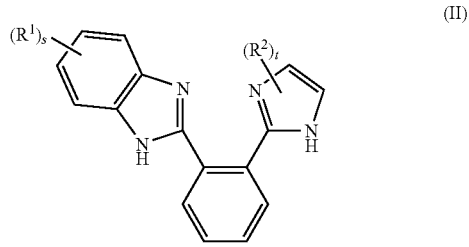

(V)

7. The compound according to claim 1, wherein each R¹ is independently selected from NH₂, OR⁷, NR⁸R⁹, and hydroxy.

8. The compound according to claim 1, wherein R¹ and R² are each independently selected from halogen.

9. The composition according to claim 4, wherein each R¹ is independently selected from NH₂, OR⁷, NR⁸R⁹, and hydroxy.

10. The composition according to claim 4, wherein R¹ and R² are independently selected from halogen.

11. The compound according to claim 1 of Formula II:

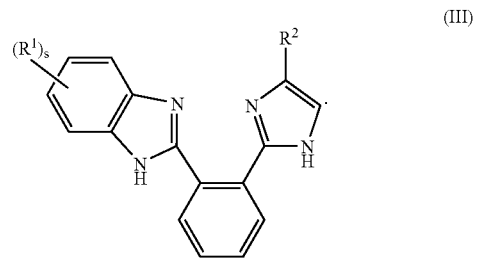

(II)

wherein

R¹ and R² are members independently selected from H, NH₂, alkyl amines, aryl amines, carboxyl, C(O)NH₂, alkyl amides, aryl amides, sulfonamides, thioureas, esters, halogens, alkoxy, carbamate, ether, hydroxy substituted or unsubstituted alkyl and ketone; or two R¹ groups together with the atoms to which they are joined form an unsubstituted 5- to 7-membered ring.

12. The compound according to claim 11 of Formula III:

(III)

13. The compound according to claim 12 of Formula IV:

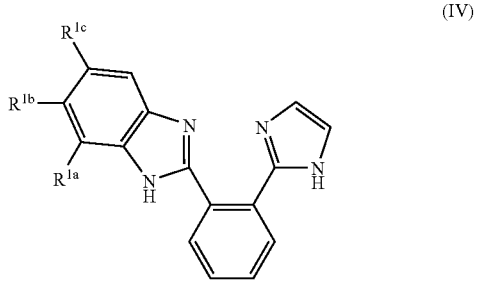

(IV)

wherein $R^{1a}$, $R^{1b}$ and $R^{1c}$ are members independently selected from H, NH₂, alkyl l amines, aryl amines, carboxyl, C(O)NH₂, alkyl amides, aryl amides, sulfonamides, thioureas, esters, halogens, alkoxy, carbamate, ether, hydroxy substituted or unsubstituted alkyl and ketone; or $R^{1b}$ and $R^{1c}$ together with the atoms to which they are joined form a substituted or unsubstituted 5- to 7-membered ring.

14. The compound according to claim 13, wherein $R^{1b}$ and $R^{1c}$ are combined to form an oxygen-containing heterocycle.

15. The compound according to claim 1 of the formula:

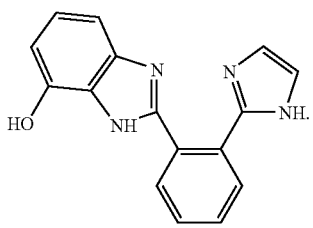

16. The compound according to claim 13, wherein $R^{1a}$ is H and $R^{1c}$ is H.

17. The compound according to claim 1 of the formula:

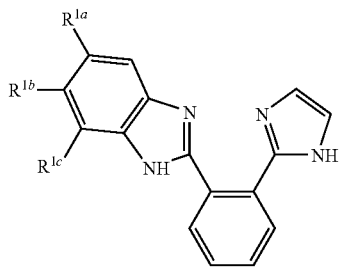

wherein $R^{1a}$ and $R^{1c}$ are each independently selected from the group consisting of H, $NH_2$, alkyl amines, aryl amines, carboxyl, $C(O)NH_2$, alkyl amides, aryl amides, sulfonamides, thioureas, esters, halogens, alkoxy, carbamate, ether, hydroxy substituted or unsubstituted alkyl and ketone; and $R^{1b}$ is selected from H, $-NH_2$, $-OCH_3$,

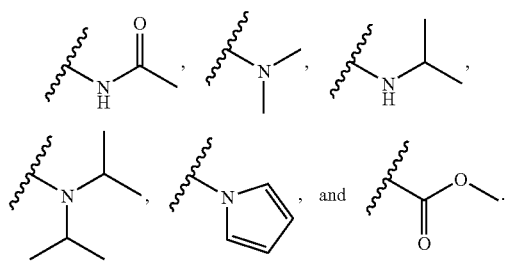

18. The compound according to claim 1 and a pharmaceutically acceptable salts of thereof, wherein said compound is a structure selected from the group consisting of:

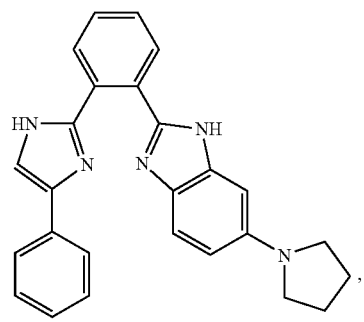
14
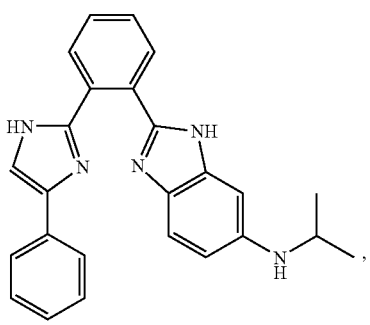
15
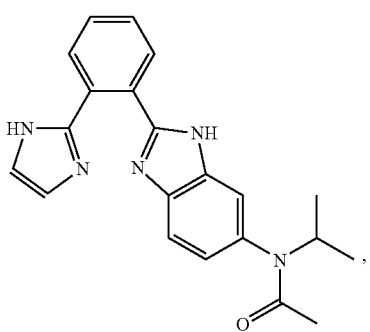
16
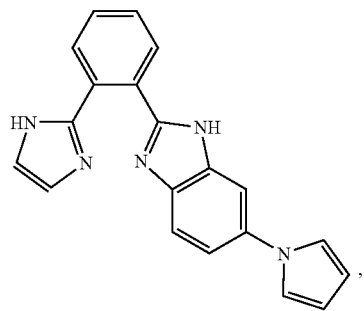
17
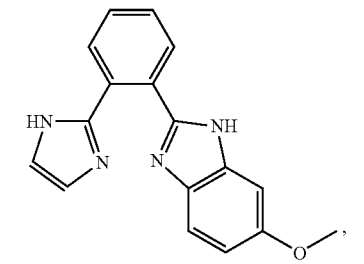
18
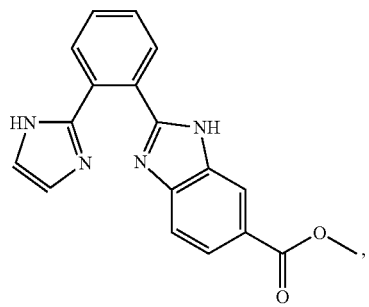
19
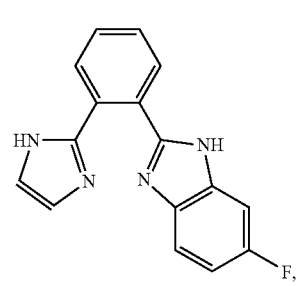
21
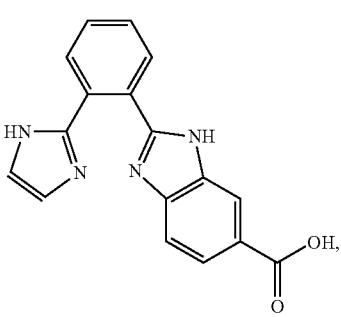
22
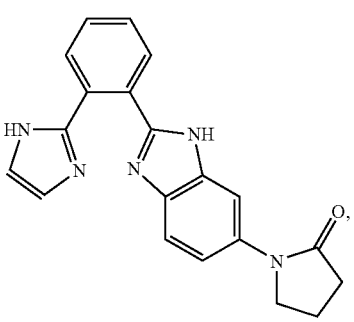
23
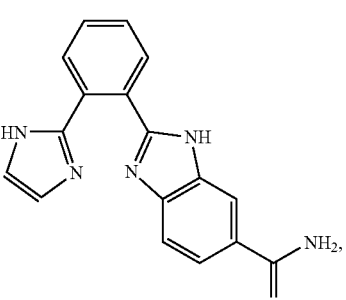
24

| 38 | 43 |
| 39 | 44 |
| 40 | 45 |
| 41 | 46 |
| 42 | 47 |

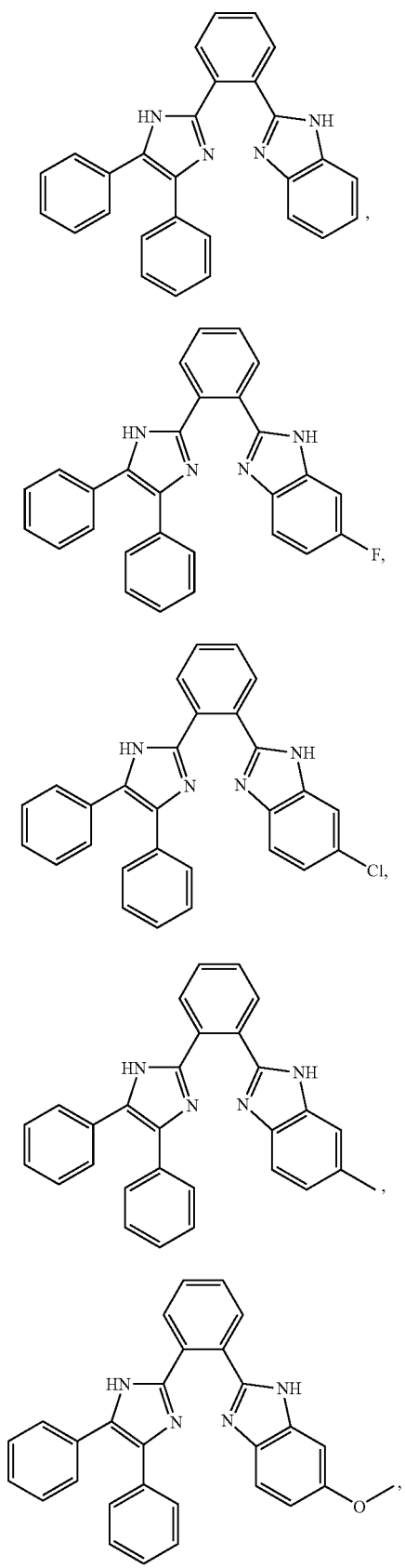
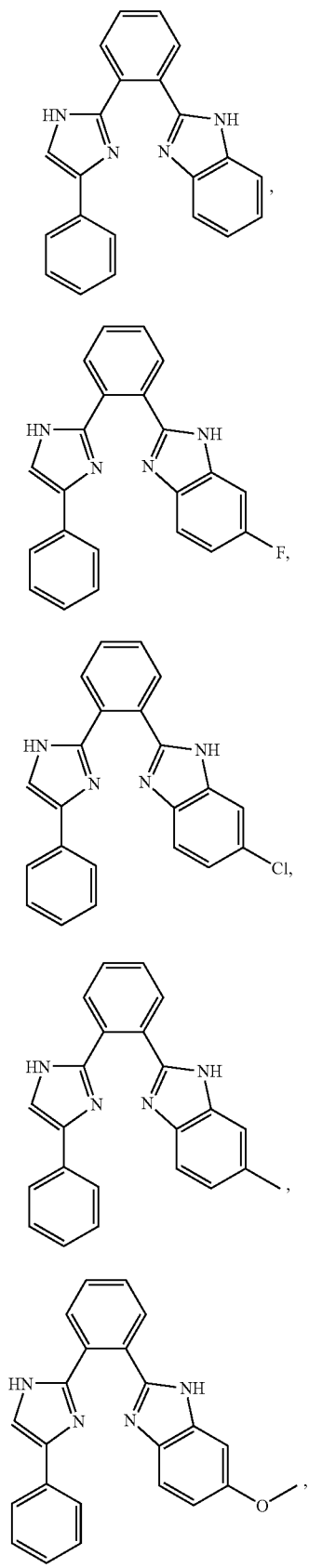

41

-continued

42

-continued

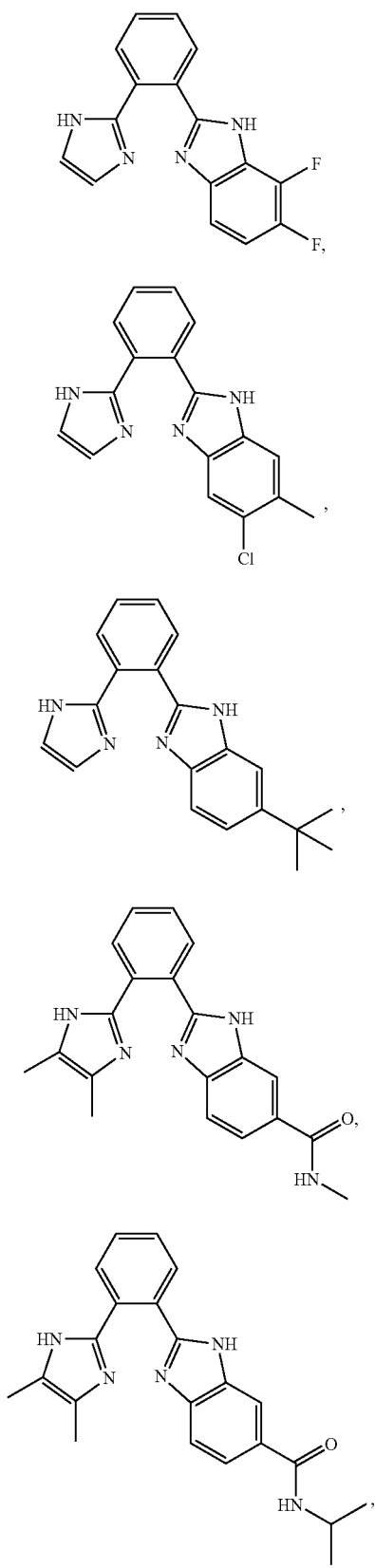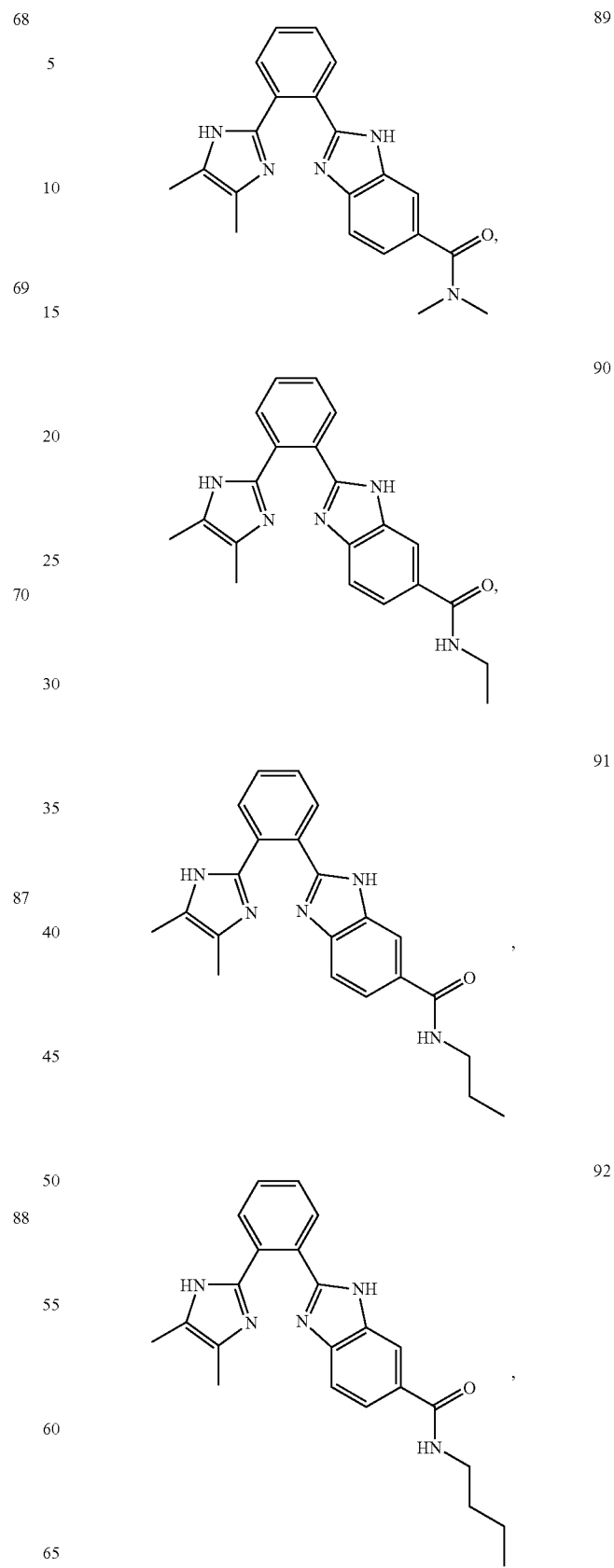

-continued

-continued
102 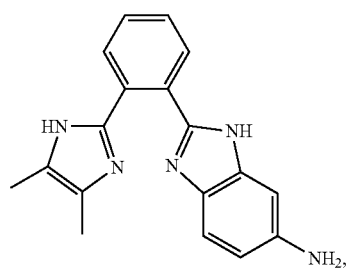
103 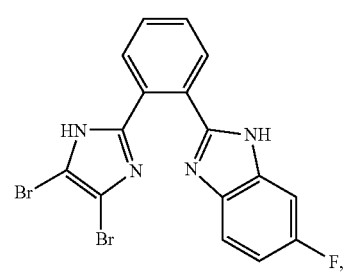
104 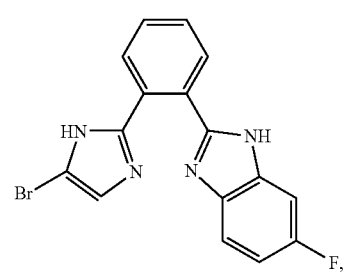
105 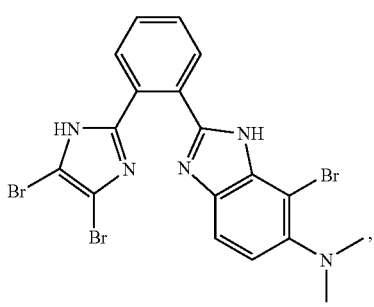
106 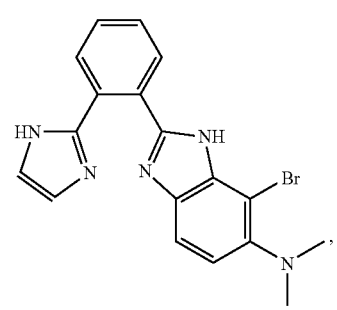
-continued
107 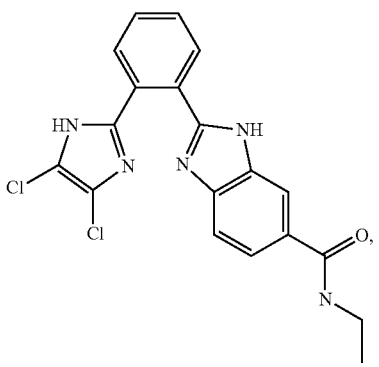
108 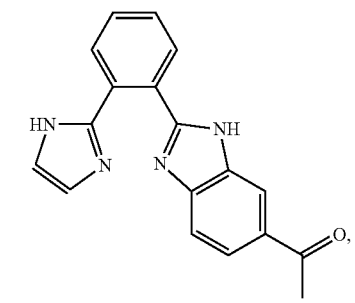
109 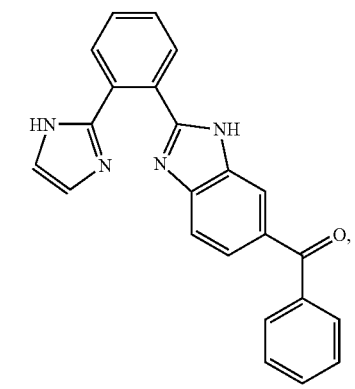
110 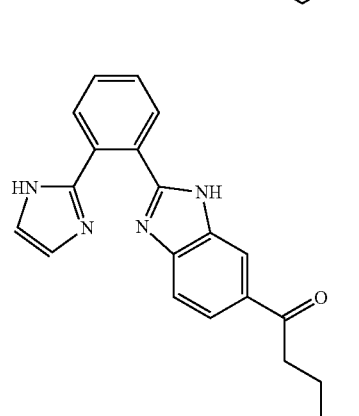

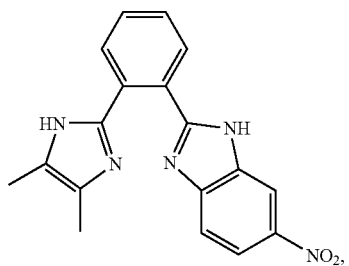
111
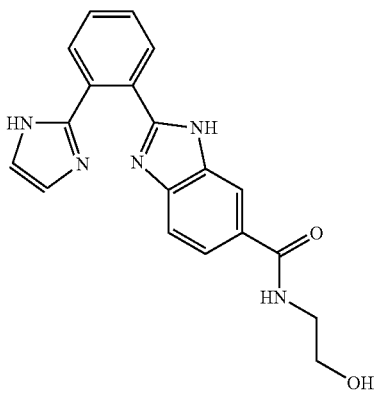
116
112
117
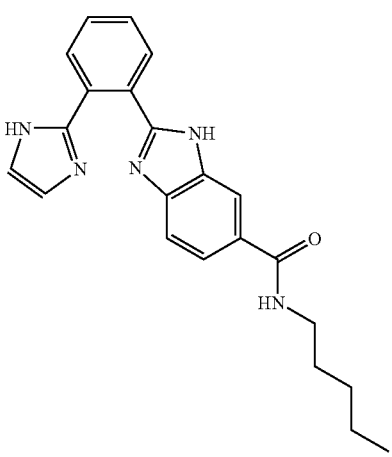
113
115
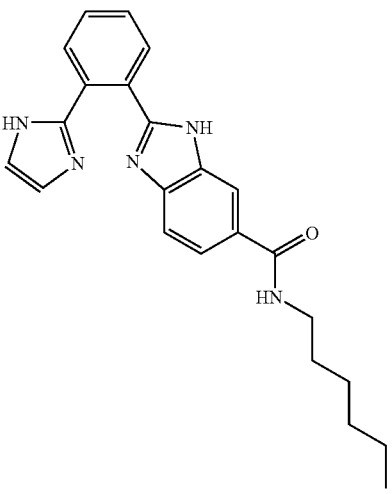
118

-continued

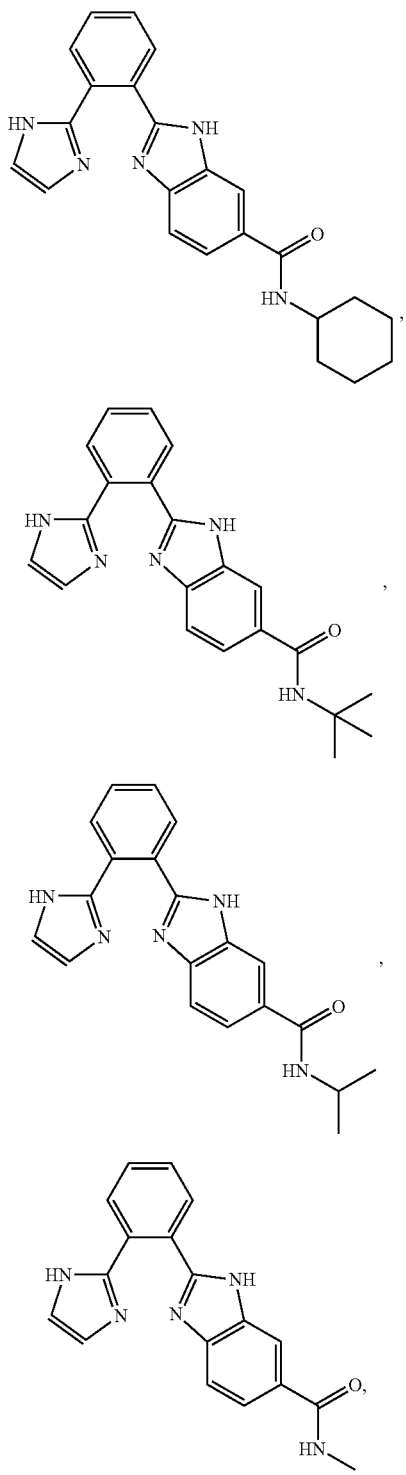

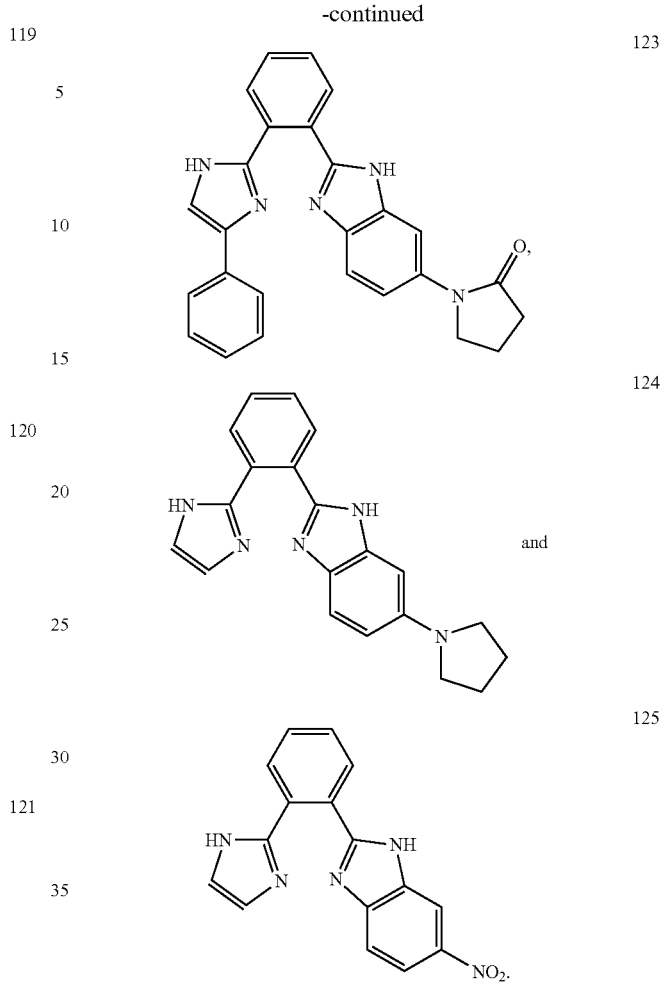

19. A composition comprising a pharmaceutically acceptable excipient and a compound of claim 12.

20. A composition comprising a pharmaceutically acceptable excipient and a compound of claim 13.

21. A composition comprising a pharmaceutically acceptable excipient and a compound of claim 14.

22. A composition comprising a pharmaceutically acceptable excipient and a compound of claim 15.

23. A composition comprising a pharmaceutically acceptable excipient and a compound of claim 16.

24. A composition comprising a pharmaceutically acceptable excipient and a compound of claim 17.

25. A composition comprising a pharmaceutically acceptable excipient and a compound of claim 18.

* * * * *